United States Patent
Almendro Barreda et al.

(10) Patent No.: US 12,062,016 B2
(45) Date of Patent: *Aug. 13, 2024

(54) AUTOMATED CLINICAL DOCUMENTATION SYSTEM AND METHOD

(71) Applicant: Microsoft Technology Licensing, LLC, Redmond, WA (US)

(72) Inventors: Daniel Paulino Almendro Barreda, London (GB); Dushyant Sharma, Mountain House, CA (US); Joel Praveen Pinto, Aachen (DE); Uwe Helmut Jost, Groton, MA (US); Patrick A. Naylor, Reading (GB)

(73) Assignee: Microsoft Technology Licensing, LLC, Redmond, WA (US)

( * ) Notice: Subject to any disclaimer, the term of this patent is extended or adjusted under 35 U.S.C. 154(b) by 70 days.

This patent is subject to a terminal disclaimer.

(21) Appl. No.: 17/678,791

(22) Filed: Feb. 23, 2022

(65) Prior Publication Data

US 2022/0180318 A1 Jun. 9, 2022

Related U.S. Application Data

(63) Continuation of application No. 16/271,329, filed on Feb. 8, 2019, now Pat. No. 11,295,272.

(Continued)

(51) Int. Cl.
*G16H 10/60* (2018.01)
*G06F 3/16* (2006.01)
(Continued)

(52) U.S. Cl.
CPC ............. *G06Q 10/10* (2013.01); *G06F 3/165* (2013.01); *G06F 40/117* (2020.01); *G06F 40/30* (2020.01);
(Continued)

(58) Field of Classification Search
CPC ........ G06Q 10/10; G06Q 50/22; G06F 3/165; G06F 40/117; G06F 40/30; G06F 40/151;
(Continued)

(56) References Cited

U.S. PATENT DOCUMENTS 5,357,427 A 10/1994 Langen et al.
8,132,104 B2 3/2012 Ash et al.
(Continued)

FOREIGN PATENT DOCUMENTS

WO 9844484 A1 10/1998
WO 2005093716 A1 10/2005
(Continued)

OTHER PUBLICATIONS

Ashtosh Sapru; Sree Harsha Yella; Hervé Bourlard; "Improving speaker diarization using social role information," 2014 IEEE International Conference on Acoustic, Speech and Signal Processing (ICASSP) (Year: 2014).*
(Continued)

*Primary Examiner* — Joshua B Blanchette
(74) *Attorney, Agent, or Firm* — Brian J. Colandreo; Heath M. Sargeant; Holland & Knight LLP

(57) ABSTRACT

A method, computer program product, and computing system for obtaining encounter information of a patient encounter, wherein the encounter information includes machine vision encounter information; and processing the encounter information to generate an encounter transcript.

20 Claims, 9 Drawing Sheets

Related U.S. Application Data

(60) Provisional application No. 62/638,809, filed on Mar. 5, 2018.

(51) Int. Cl.

| | |
|---|---|
| *G06F 40/117* | (2020.01) |
| *G06F 40/30* | (2020.01) |
| *G06Q 10/10* | (2023.01) |
| *G06T 7/20* | (2017.01) |
| *G10L 15/22* | (2006.01) |
| *G10L 15/26* | (2006.01) |
| *G10L 15/30* | (2013.01) |
| *G10L 25/45* | (2013.01) |
| *G10L 25/51* | (2013.01) |
| *G16H 10/20* | (2018.01) |
| *G16H 10/40* | (2018.01) |
| *G16H 15/00* | (2018.01) |
| *G16H 50/70* | (2018.01) |
| *H04R 1/40* | (2006.01) |
| *H04R 3/00* | (2006.01) |

(52) U.S. Cl.
CPC .............. *G06T 7/20* (2013.01); *G10L 15/22* (2013.01); *G10L 15/26* (2013.01); *G10L 15/30* (2013.01); *G10L 25/45* (2013.01); *G10L 25/51* (2013.01); *G16H 10/20* (2018.01); *G16H 10/40* (2018.01); *G16H 10/60* (2018.01); *G16H 15/00* (2018.01); *G16H 50/70* (2018.01); *H04R 1/406* (2013.01); *H04R 3/005* (2013.01); *G06T 2207/30196* (2013.01)

(58) Field of Classification Search
CPC .............. G06F 40/279; G06T 7/20; G06T 2207/30196; G10L 15/22; G10L 15/26; G10L 15/30; G10L 25/45; G10L 25/51; G16H 10/20; G16H 10/40; G16H 10/60; G16H 15/00; G16H 50/70; G16H 30/40; G16H 80/00; H04R 1/406; H04R 3/005
See application file for complete search history.

(56) References Cited

U.S. PATENT DOCUMENTS

| | | | |
|---|---|---|---|
| 8,589,379 | B2 | 11/2013 | Hirasawa |
| 9,104,985 | B2 | 8/2015 | Drucker et al. |
| 9,479,931 | B2 | 10/2016 | Ortiz et al. |
| 9,509,676 | B1 | 11/2016 | Johnson et al. |
| 9,679,107 | B2 | 6/2017 | Cardoza et al. |
| 10,212,588 | B2 | 2/2019 | Grim et al. |
| 10,354,054 | B2 | 7/2019 | Kobres et al. |
| 10,546,655 | B2 | 1/2020 | Owen et al. |
| 10,650,824 | B1 | 5/2020 | Kesharaju et al. |
| 10,691,783 | B2 | 6/2020 | Frempong et al. |
| 10,701,081 | B2 | 6/2020 | Grim et al. |
| 10,803,436 | B2 | 10/2020 | Kobres et al. |
| 10,957,427 | B2 | 3/2021 | Owen et al. |
| 10,957,428 | B2 | 3/2021 | Owen et al. |
| 10,978,187 | B2 | 4/2021 | Owen et al. |
| 11,043,288 | B2 | 6/2021 | Gallopyn et al. |
| 11,074,996 | B2 | 7/2021 | Gallopyn et al. |
| 11,101,022 | B2 | 8/2021 | Owen |
| 11,101,023 | B2 | 8/2021 | Gallopyn et al. |
| 11,114,186 | B2 | 9/2021 | Owen |
| 11,177,034 | B2 | 11/2021 | Lyman et al. |
| 11,238,226 | B2 | 2/2022 | Vozila et al. |
| 11,250,382 | B2 | 2/2022 | Sharma et al. |
| 11,250,383 | B2 | 2/2022 | Sharma et al. |
| 11,257,576 | B2 | 2/2022 | Owen et al. |
| 11,270,261 | B2 | 3/2022 | Vozila |
| 11,295,838 | B2 | 4/2022 | Owen et al. |
| 11,295,839 | B2 | 4/2022 | Owen et al. |
| 11,316,865 | B2 | 4/2022 | Gallopyn et al. |
| 11,322,231 | B2 | 5/2022 | Owen et al. |
| 11,368,454 | B2 | 6/2022 | Whaley et al. |
| 11,402,976 | B1 | 8/2022 | Palamadai et al. |
| 11,483,707 | B2 | 10/2022 | Leblang et al. |
| 11,538,567 | B2 | 12/2022 | Davies |
| 2001/0044588 | A1 | 11/2001 | Mault |
| 2003/0051214 | A1 | 3/2003 | Graham et al. |
| 2003/0105631 | A1 | 6/2003 | Habte |
| 2005/0154588 | A1 | 7/2005 | Janas et al. |
| 2006/0061595 | A1 | 3/2006 | Goede et al. |
| 2006/0069545 | A1 | 3/2006 | Wu et al. |
| 2006/0106645 | A1 | 5/2006 | Bergelson et al. |
| 2008/0222734 | A1 | 9/2008 | Redlich et al. |
| 2008/0243544 | A1 | 10/2008 | Cafer |
| 2009/0023555 | A1 | 1/2009 | Raymond |
| 2009/0089082 | A1 | 4/2009 | Heckerman et al. |
| 2009/0132276 | A1 | 5/2009 | Petera |
| 2009/0157385 | A1 | 6/2009 | Tian et al. |
| 2009/0178144 | A1 | 7/2009 | Redlich et al. |
| 2009/0248444 | A1 | 10/2009 | Harnick |
| 2009/0304254 | A1 | 12/2009 | Yoshida |
| 2010/0191519 | A1 | 7/2010 | Morton et al. |
| 2011/0254954 | A1 | 10/2011 | Lee |
| 2012/0041949 | A1 | 2/2012 | Hirasawa et al. |
| 2012/0081504 | A1 | 4/2012 | Ng et al. |
| 2012/0173269 | A1 | 7/2012 | Omidi |
| 2012/0173278 | A1 | 7/2012 | Herbst et al. |
| 2012/0197648 | A1 | 8/2012 | Moloney |
| 2012/0209625 | A1 | 8/2012 | Armstrong et al. |
| 2012/0330876 | A1 | 12/2012 | Bryce |
| 2013/0238330 | A1* | 9/2013 | Casella dos Santos ..................... G16H 10/60 704/235 |
| 2013/0246329 | A1 | 9/2013 | Pasquero et al. |
| 2013/0317838 | A1 | 11/2013 | Schoenberg |
| 2013/0325488 | A1 | 12/2013 | Carter et al. |
| 2014/0013219 | A1 | 1/2014 | Liu |
| 2014/0047375 | A1 | 2/2014 | Koll et al. |
| 2014/0136973 | A1 | 5/2014 | Kumar et al. |
| 2014/0164994 | A1 | 6/2014 | Myslinski |
| 2014/0188516 | A1 | 7/2014 | Kamen et al. |
| 2014/0253876 | A1 | 9/2014 | Klin |
| 2014/0275928 | A1 | 9/2014 | Acquista et al. |
| 2014/0278448 | A1 | 9/2014 | Sadeghi et al. |
| 2014/0282008 | A1 | 9/2014 | Verard |
| 2014/0358585 | A1 | 12/2014 | Reiner |
| 2015/0106123 | A1 | 4/2015 | Amarasingham |
| 2015/0149207 | A1 | 5/2015 | O'keefe |
| 2015/0154358 | A1 | 6/2015 | Anderson et al. |
| 2015/0182296 | A1 | 7/2015 | Daon |
| 2015/0220637 | A1 | 8/2015 | Goetz |
| 2016/0063191 | A1 | 3/2016 | Vesto et al. |
| 2016/0110350 | A1 | 4/2016 | Waibel |
| 2016/0210429 | A1 | 7/2016 | Ortiz et al. |
| 2016/0239617 | A1 | 8/2016 | Farooq et al. |
| 2016/0364526 | A1 | 12/2016 | Reicher et al. |
| 2016/0366299 | A1 | 12/2016 | Sato |
| 2017/0006135 | A1 | 1/2017 | Siebel et al. |
| 2017/0039502 | A1 | 2/2017 | Guman |
| 2017/0083214 | A1 | 3/2017 | Furesjöet al. |
| 2017/0098051 | A1 | 4/2017 | Balram |
| 2017/0185716 | A1 | 6/2017 | Rodriguez et al. |
| 2017/0277993 | A1 | 9/2017 | Beaver |
| 2017/0287031 | A1 | 10/2017 | Barday |
| 2017/0295075 | A1 | 10/2017 | Roebuck |
| 2017/0300648 | A1 | 10/2017 | Charlap |
| 2018/0158555 | A1 | 6/2018 | Cashman et al. |
| 2019/0051374 | A1 | 2/2019 | Vozila et al. |
| 2019/0051375 | A1 | 2/2019 | Owen et al. |
| 2019/0051376 | A1 | 2/2019 | Gallopyn et al. |
| 2019/0051379 | A1 | 2/2019 | Owen et al. |
| 2019/0051380 | A1 | 2/2019 | Owen et al. |
| 2019/0051394 | A1 | 2/2019 | Owen et al. |
| 2019/0066823 | A1 | 2/2019 | Owen |
| 2019/0121532 | A1 | 4/2019 | Strader et al. |
| 2019/0272145 | A1 | 9/2019 | Sharma et al. |
| 2019/0272147 | A1 | 9/2019 | Vozila et al. |
| 2019/0272827 | A1 | 9/2019 | Vozila |

(56) References Cited

U.S. PATENT DOCUMENTS

| | | | |
|---|---|---|---|
| 2019/0272895 A1 | 9/2019 | Vozila et al. |
| 2019/0272896 A1 | 9/2019 | Vozila et al. |
| 2019/0272897 A1 | 9/2019 | Öz et al. |
| 2019/0272899 A1 | 9/2019 | Drexel et al. |
| 2019/0272900 A1 | 9/2019 | Jancsary et al. |
| 2019/0272902 A1 | 9/2019 | Vozila et al. |
| 2019/0272905 A1 | 9/2019 | Almendro Barreda et al. |
| 2019/0272906 A1 | 9/2019 | Vozila et al. |
| 2020/0160951 A1 | 5/2020 | Owen et al. |
| 2020/0279107 A1 | 9/2020 | Staar et al. |
| 2020/0342966 A1 | 10/2020 | Stern |
| 2021/0210180 A1 | 7/2021 | Owen et al. |
| 2021/0210181 A1 | 7/2021 | Owen et al. |
| 2021/0210200 A1 | 7/2021 | Gallopyn et al. |
| 2021/0233634 A1 | 7/2021 | Owen et al. |
| 2021/0233652 A1 | 7/2021 | Owen et al. |
| 2021/0243412 A1 | 8/2021 | Owen et al. |
| 2021/0407635 A1 | 12/2021 | Owen |
| 2022/0051772 A1 | 2/2022 | Gallopyn et al. |
| 2022/0130502 A1 | 4/2022 | Vozila et al. |
| 2022/0208322 A1 | 6/2022 | Owen et al. |
| 2022/0210161 A1 | 6/2022 | Gallopyn et al. |
| 2022/0319653 A1 | 10/2022 | Owen et al. |
| 2023/0014971 A1 | 1/2023 | Drexel et al. |
| 2023/0021529 A1 | 1/2023 | Bhattacherjee et al. |
| 2023/0092558 A1 | 3/2023 | Vozila et al. |
| 2023/0290023 A1 | 9/2023 | Tsunomori et al. |

FOREIGN PATENT DOCUMENTS

| | | | |
|---|---|---|---|
| WO | 2013118510 A1 | 8/2013 |
| WO | 2015021208 A1 | 2/2015 |
| WO | 2016149794 A1 | 9/2016 |
| WO | 2017100334 A1 | 6/2017 |
| WO | 2018132336 A1 | 7/2018 |

OTHER PUBLICATIONS

"Final Office Action Issued in U.S. Appl. No. 16/058,803", Mailed Date: May 18, 2022, 12 Pages.
"Non Final Office Action Issued in U.S. Appl. No. 16/058,803", Mailed Date: Sep. 21, 2022, 11 Pages.
"Final Office Action Issued in U.S. Appl. No. 16/058,826", Mailed Date: Oct. 21, 2021, 24 Pages.
"Final Office Action Issued in U.S. Appl. No. 16/058,826", Mailed Date: Aug. 19, 2022, 37 Pages.
"Non Final Office Action Issued in U.S. Appl. No. 16/058,826", Mailed Date: Mar. 29, 2022, 37 Pages.
"Notice of Allowance Issued in U.S. Appl. No. 16/058,829", Mailed Date : Jun. 3, 2022, 9 Pages.
"Non Final Office Action Issued in U.S. Appl. No. 16/058,871", Mailed Date: Dec. 3, 2018, 9 Pages.
"Final Office Action Issued in U.S. Appl. No. 16/058,883", Mailed Date: Oct. 29, 2021, 22 Pages.
"Notice of Allowance Issued in U.S. Appl. No. 16/058,883", Mailed Date: Jun. 2, 2022, 2 Pages.
"Notice of Allowance Issued in U.S. Appl. No. 16/058,883", Mailed Date: Mar. 25, 2022, 9 Pages.
"Final Office Action Issued in U.S. Appl. No. 16/058,894", Mailed Date: Oct. 29, 2021, 25 Pages.
"Final Office Action Issued in U.S. Appl. No. 16/058,894", Mailed Date: Aug. 17, 2022, 45 Pages.
"Non Final Office Action Issued in U.S. Appl. No. 16/058,894", Mailed Date: Mar. 31, 2022, 44 Pages.
"Final Office Action Issued in U.S. Appl. No. 16/058,914", Mailed Date: Oct. 29, 2021, 25 Pages.
"Non Final Office Action Issued in U.S. Appl. No. 16/058,914", Mailed Date: May 24, 2022, 9 Pages.
"Notice of Allowance Issued in U.S. Appl. No. 16/058,914", Mailed Date: Sep. 14, 2022, 11 Pages.
"Notice of Allowance Issued in U.S. Appl. No. 16/058,914", Mailed Date: Mar. 30, 2022, 12 Pages.
"Final Office Action Issued in U.S. Appl. No. 16/058,925", Mailed Date: Oct. 20, 2022, 23 Pages.
"Final Office Action Issued in U.S. Appl. No. 16/058,925", Mailed Date: Oct. 29, 2021, 25 Pages.
"Non Final Office Action Issued in U.S. Appl. No. 16/058,925", Mailed Date: Mar. 30, 2022, 21 Pages.
"Advisory Action Issued in U.S. Appl. No. 16/058,936", Mailed Date: Aug. 19, 2020, 5 Pages.
"Notice of Allowance Issued in U.S. Appl. No. 16/058,951", Mailed Date: Nov. 15, 2019, 11 Pages.
"Final Office Action Issued in U.S. Appl. No. 16/059,818", Mailed Date: Apr. 7, 2020, 7 Pages.
"Advisory Action Issued In U.S. Appl. No. 16/059,895", Mailed Date: Sep. 10, 2020, 5 Pages.
"Final Office Action Issued in U.S. Appl. No. 16/059,967", Mailed Date: Apr. 1, 2022, 10 Pages.
"Advisory Action Issued In U.S. Appl. No. 16/059,974", Mailed Date: Sep. 15, 2020, 5 Pages.
"Non Final Office Action Issued in U.S. Appl. No. 16/059,974", Mailed Date: Dec. 18, 2020, 20 Pages.
"Notice of Allowance Issued in U.S. Appl. No. 16/059,974", Mailed Date: Feb. 4, 2022, 11 Pages.
"Advisory Action Issued In U.S. Appl. No. 16/059,986", Mailed Date: Sep. 15, 2020, 5 Pages.
"Final Office Action issued in related U.S. Appl. No. 16/100,030", Mailed Date: May 8, 2020, 10 Pages.
"Notice of Allowance Issued in U.S. Appl. No. 16/100,030", Mailed Date: Jan. 28, 2021, 6 Pages.
"Notice of Allowance Issued in U.S. Appl. No. 16/192,358", Mailed Date: Dec. 8, 2021, 8 Pages.
"Notice of Allowance Issued in U.S. Appl. No. 16/270,888", Mailed Date: Jul. 13, 2022, 8 Pages.
"Non Final Office Action Issued in U.S. Appl. No. 16/271,029", Mailed Date: Jun. 21, 2022, 30 Pages.
"Final Office Action Issued in U.S. Appl. No. 16/292,877", Mailed Date: Nov. 14, 2022, 10 Pages.
"Non Final Office Action Issued in U.S. Appl. No. 16/292,877", Mailed Date: May 2, 2022, 10 Pages.
"Final Office Action Issued in U.S. Appl. No. 16/292,893", Mailed Date: Jul. 28, 2022, 39 Pages.
"Non Final Office Action Issued in U.S. Appl. No. 16/292,893", Mailed Date: Mar. 29, 2022, 37 Pages.
"Non Final Office Action Issued in U.S. Appl. No. 16/292,895", Mailed Date: May 17, 2022, 17 Pages.
"Final Office Action Issued in U.S. Appl. No. 16/292,973", Mailed Date: Oct. 28, 2022, 27 Pages.
"Non Final Office Action Issued in U.S. Appl. No. 16/292,973", Mailed Date: Apr. 1, 2022, 26 Pages.
"Non Final Office Action Issued in U.S. Appl. No. 16/293,032", Mailed Date: Apr. 5, 2022, 37 Pages.
"Notice of Allowance Issued in U.S. Appl. No. 16/293,032", Mailed Date: Jul. 25, 2022, 11 Pages.
"Non Final Office Action Issued in U.S. Appl. No. 16/588,475", Mailed Date: Sep. 16, 2022, 17 Pages.
"Non Final Office Action Issued in U.S. Appl. No. 16/588,897", Mailed Date: Mar. 31, 2022, 6 Pages.
"Notice of Allowance Issued in U.S. Appl. No. 16/588,897", Mailed Date: Sep. 2, 2022, 8 Pages.
"Notice of Allowance Issued in U.S. Appl. No. 17/084,448", Mailed Date: Jan. 26, 2022, 5 Pages.
"Notice of Allowance Issued in U.S. Appl. No. 17/210,052", Mailed Date : Feb. 18, 2022, 7 Pages.
"Notice of Allowance Issued in U.S. Appl. No. 17/210,052", Mailed Date: Sep. 9, 2022, 8 Pages.
"Non Final Office Action Issued in U.S. Appl. No. 17/210,120", Mailed Date: Nov. 1, 2021, 14 Pages.
"Non Final Office Action Issued in U.S. Appl. No. 17/210,233", Mailed Date: Oct. 23, 2023, 47 Pages.
"Non Final Office Action Issued in U.S. Appl. No. 17/846,355", Mailed Date: Sep. 27, 2023, 16 Pages.

(56) References Cited

OTHER PUBLICATIONS

"Non Final Office Action Issued in U.S. Appl. No. 17/955,693", Mailed Date: Nov. 9, 2023, 8 Pages.
Notice of Allowance mailed on Feb. 14, 2024, in U.S. Appl. No. 17/571,799, 7 pages.
Notice of Allowance mailed on Jan. 31, 2024 in U.S. Appl. No. 17/846,355, 8 Pages.
Shen, et al., "Auto-encoding twin-bottleneck hashing", In Proceedings of the IEEE/CVF Conference on Computer Vision and Pattern Recognition, Jun. 13, 2020, pp. 2818-2827.
"Notice of Allowance Issued in U.S. Appl. No. 17/210,120", Mailed Date: Jun. 10, 2022, 7 Pages.
Pusateri, et al., "A Mostly Data-Driven Approach to Inverse Text Normalization", In Proceedings of Interspeech, Aug. 20, 2017, pp. 2784-2788.
"Notice of Allowance Issued in U.S. Appl. No. 17/210,120", Mailed Date: Mar. 1, 2022, 8 Pages.
"Notice of Allowance Issued in U.S. Appl. No. 17/467,688", Mailed Date: Oct. 6, 2022, 9 Pages.
"Non Final Office Action Issued in U.S. Appl. No. 17/571,799", Mailed Date: Dec. 6, 2022, 26 Pages.
"Non Final Office Action Issued in U.S. Appl. No. 17/696,165", Mailed Date: Nov. 25, 2022, 7 Pages.
"Office Action Issued in European Patent Application No. 18844675.1", Mailed Date: Mar. 4, 2022, 6 Pages.
"Extended European Search Report Issued in European Application No. 18844829.4", Mailed Date: Apr. 30, 2021, 9 Pages.
"Extended European Search Report Issued in Application No. 19763338.1", Mailed Date: Apr. 4, 2022, 8 Pages.
"European Extended Search Report for Application No. 19763474.4", Mailed Date: Apr. 8, 2022, 8 Pages.
"Extended European Search Report Issued in Application No. 19763475.1", Mailed Date: Apr. 12, 2022, 10 Pages.
"Search Report Issued in European Patent Application No. 19763477.7", Mailed Date: Mar. 28, 2022, 10 Pages.
"Search Report Issued in European Patent Application No. 19763600.4", Mailed Date: Mar. 31, 2022, 9 Pages.
"Search Report Issued in European Patent Application No. 19763678.0", Mailed Date: Mar. 25, 2022, 8 Pages.
"Search Report Issued in European Patent Application No. 19763834.9", Mailed Date: Dec. 10, 2021, 9 Pages.
"Search Report Issued in European Patent Application No. 19764329.9", Mailed Date: Dec. 14, 2021, 13 Pages.
Hoof, et al., "Ageing-in-place with the use of ambient intelligence technology: Perspectives of older users", In International Journal of Medical Informatics, vol. 80, Issue 5, May 1, 2011, pp. 310-331.
"International Search Report and Written Opinion Issued in PCT Application No. PCT/US21/056274", Mailed Date: Dec. 7, 2021, 7 Pages.
"International Search Report and Written Opinion Issued in PCT Application No. PCT/US22/021375", Mailed Date: Jul. 26, 2022, 8 Pages.
"International Search Report and Written Opinion Issued in PCT Application No. PCT/US22/021393", Mailed Date: Sep. 2, 2022, 12 Pages.
"Invitation To Pay Additional Fees Issued in PCT Application No. PCT/US22/021393", Mailed Date: Jun. 24, 2022, 2 Pages.
"International Search Report and Written Opinion Issued in PCT Application No. PCT/US22/021412", Mailed Date: Sep. 2, 2022, 11 Pages.
"Invitation To Pay Additional Fees Issued in PCT Application No. PCT/US22/021412", Mailed Date: Jun. 24, 2022, 2 Pages.
"International Search Report and Written Opinion Issued in PCT Application No. PCT/US22/021419", Mailed Date: Sep. 23, 2022, 13 Pages.
"Invitation To Pay Additional Fees Issued in PCT Application No. PCT/US22/021419", Mailed Date: Jul. 5, 2022, 2 Pages.
"International Search Report and Written Opinion Issued in PCT Application No. PCT/US22/021422", Mailed Date: Sep. 2, 2022, 11 Pages.
"Invitation To Pay Additional Fees Issued in PCT Application No. PCT/US22/021422", Mailed Date: Jun. 24, 2022, 2 Pages.
"Notice of Allowance Issued in U.S. Appl. No. 16/058,914", Mailed Date: Jan. 5, 2023, 11 Pages.
"Final Office Action Issued in U.S. Appl. No. 16/058,803", Mailed Date: Mar. 20, 2023, 12 Pages.
"Final Office Action Issued in U.S. Appl. No. 16/292,895", Mailed Date: Jan. 5, 2023, 17 Pages.
"Notice of Allowance Issued in U.S. Appl. No. 17/210,052", Mailed Date: Jan. 30, 2023, 5 Pages.
"Office Action Issued in European Patent Application No. 18843329.6", Mailed Date: Feb. 24, 2023, 5 Pages.
Shivappa, et al., "Person Tracking With Audio-visual Cues Using The Iterative Decoding Framework", In Proceedings of the IEEE Fifth International Conference on Advanced Video and Signal Based Surveillance, Sep. 1, 2008, pp. 260-267.
Watanabe, et al., "Hybrid CTC/Attention Architecture for End-to-End Speech Recognition", In Journal of IEEE Selected Topics in Signal Processing, vol. 11, Issue 8, Dec. 2017, pp. 1240-1253.
"Non Final Office Action Issued in U.S. Appl. No. 17/991,234", Mailed Date: Mar. 14, 2023, 42 Pages.
"Notice of Allowance Issued in U.S. Appl. No. 17/210,052", Mailed Date: Apr. 10, 2023, 5 Pages.
"Final Office Action Issued in U.S. Appl. No. 17/571,799", Mailed Date: Apr. 25, 2023, 31 Pages.
"Notice of Allowance Issued in U.S. Appl. No. 17/696,165", Mailed Date: Apr. 26, 2023, 7 Pages.
"Notice of Allowance Issued in European Patent Application No. 18843586.1", Mailed Date: Mar. 14, 2023, 8 Pages.
"Final Office Action Issued in U.S. Appl. No. 17/991,234", Mailed Date: Jul. 11, 2023, 35 Pages.
"Notice of Allowance Issued In European Patent Application No. 18843586.1", Mailed Date: Jun. 9, 2023, 2 Pages.
"Non Final Office Action Issued in U.S. Appl. No. 17/571,799", Mailed Date: Jul. 27, 2023, 29 Pages.
Non-Final Office Action mailed on Dec. 11, 2023, in U.S. Appl. No. 17/697,593, 23 Pages.
Communication 94(3) Received for European Application No. 18844406.1, mailed on Apr. 4, 2024, 11 pages.
Communication 94(3) Received for European Application No. 18844669.4, mailed on Apr. 3, 2024, 5 pages.
Communication 94(3) Received for European Application No. 18844829.4, mailed on Apr. 4, 2024, 5 pages.
Communication pursuant to Article 94(3) EPC Received for European Application No. 18843255.3, mailed on Feb. 26, 2024, 6 pages.
Communication pursuant to Article 94(3) EPC, Received for European Application No. 18843175.3, mailed on Feb. 29, 2024, 09 pages.
Communication pursuant to Article 94(3) EPC, Received for European Application No. 18843945.9, mailed on Mar. 4, 2024, 09 pages.
Communication Pursuant to Article 94(3) EPC, Received for European Application No. 18844407.9, mailed on Feb. 14, 2024, 06 pages.
Communication pursuant to Article 94(3) received in European Application No. 18844530.8, mailed on Apr. 3, 2024, 5 pages.
Communication under Rule 71(3) EPC Received for European Application No. 18845046.4, mailed on Feb. 29, 2024, 5 pages.
Non-Final Office Action mailed on Apr. 16, 2024, in U.S. Appl. No. 17/210,300, 13 pages.
Weibel, et al., "LAB-IN-A-BOX: semi-automatic tracking of activity in the medical office," Personal Ubiquitous Computing, Springer, Sep. 28, 2014, pp. 317-334.
Communication pursuant to Article 94(3) EPC Received for European Application No. 18843254.6, mailed on Mar. 26, 2024, 8 pages.
Communication pursuant to Article 94(3) Received in European Patent Application No. 18844226.3, mailed on Mar. 22, 2024, 7 pages.
Final Office Action mailed on Mar. 7, 2024, in U.S. Appl. No. 17/210,233, 54 pages.

(56) References Cited

OTHER PUBLICATIONS

Communication pursuant to Article 94(3) EPC, Received for European Application No. 18843648.9, mailed on May 2, 2024, 10 pages.
Communication pursuant to Article 94(3) received in European Application No. 18843873.3, mailed on Apr. 11, 2024, 5 pages.
Communication pursuant to Article 94(3) Received in European Patent Application No. 18845144.7, mailed on May 3, 2024, 10 pages.
Communication under Rule 71(3) EPC Received for European Application No. 18843874.1, mailed on May 10, 2024, 09 pages.
Non-Final office action mailed on Jun. 21, 2024, in U.S. Appl. No. 17/697,593, 28 pages.
Notice of Allowance mailed on Apr. 17, 2024, in U.S. Appl. No. 17/955,693, 08 pages.
Lee, et al., "Portable meeting recorder.", Proceedings of the tenth ACM international conference on Multimedia, 2002, 10 Pages.

\* cited by examiner

AUTOMATED CLINICAL DOCUMENTATION SYSTEM AND METHOD

RELATED APPLICATION(S)

This application is a continuation of U.S. Non-Provisional application Ser. No. 16/271,329, filed Feb. 8, 2019 which claims the benefit of U.S. Provisional Application No. 62/638,809, filed 5 Mar. 2018; the entire contents of which are incorporated herein by reference.

TECHNICAL FIELD

This disclosure relates to documentation systems and methods and, more particularly, to automated clinical documentation systems and methods.

BACKGROUND

As is known in the art, clinical documentation is the creation of medical records and documentation that details the medical history of medical patients. As would be expected, traditional clinical documentation includes various types of data, examples of which may include but are not limited to paper-based documents and transcripts, as well as various images and diagrams.

As the world moved from paper-based content to digital content, clinical documentation also moved in that direction, where medical records and documentation were gradually transitioned from stacks of paper geographically-dispersed across multiple locations/institutions to consolidated and readily accessible digital content.

SUMMARY OF DISCLOSURE

Video-Enhanced Speaker Identification:

In one implementation, a computer-implemented method is executed on a computing device and includes obtaining encounter information of a patient encounter, wherein the encounter information includes machine vision encounter information; and processing the encounter information to generate an encounter transcript.

One or more of the following features may be included. Obtaining encounter information of a patient encounter may include one or more of: obtaining encounter information from a medical professional; obtaining encounter information from a patient; and obtaining encounter information obtaining encounter information from a third party. The encounter information may further include audio encounter information. Processing the encounter information to generate an encounter transcript may include processing the encounter information to identify a speaker within the patient encounter. Processing the encounter information to identify a speaker within the patient encounter may include comparing the encounter information to one or more humanoid models. Processing the encounter information to generate an encounter transcript may include: processing the encounter information to associate a first potion of the encounter information with a first encounter participant; and assigning a first role to the first encounter participant. Processing the encounter information to generate an encounter transcript may include processing the encounter information to compartmentalize the encounter information into a plurality of encounter stages. At least a portion of the encounter transcript may be processed to populate at least a portion of a medical record associated with the patient encounter.

In another implementation, a computer program product resides on a computer readable medium and has a plurality of instructions stored on it. When executed by a processor, the instructions cause the processor to perform operations including obtaining encounter information of a patient encounter, wherein the encounter information includes machine vision encounter information; and processing the encounter information to generate an encounter transcript.

One or more of the following features may be included. Obtaining encounter information of a patient encounter may include one or more of: obtaining encounter information from a medical professional; obtaining encounter information from a patient; and obtaining encounter information obtaining encounter information from a third party. The encounter information may further include audio encounter information. Processing the encounter information to generate an encounter transcript may include processing the encounter information to identify a speaker within the patient encounter. Processing the encounter information to identify a speaker within the patient encounter may include comparing the encounter information to one or more humanoid models. Processing the encounter information to generate an encounter transcript may include: processing the encounter information to associate a first potion of the encounter information with a first encounter participant; and assigning a first role to the first encounter participant. Processing the encounter information to generate an encounter transcript may include processing the encounter information to compartmentalize the encounter information into a plurality of encounter stages. At least a portion of the encounter transcript may be processed to populate at least a portion of a medical record associated with the patient encounter.

In another implementation, a computing system includes a processor and memory is configured to perform operations including obtaining encounter information of a patient encounter, wherein the encounter information includes machine vision encounter information; and processing the encounter information to generate an encounter transcript.

One or more of the following features may be included. Obtaining encounter information of a patient encounter may include one or more of: obtaining encounter information from a medical professional; obtaining encounter information from a patient; and obtaining encounter information obtaining encounter information from a third party. The encounter information may further include audio encounter information. Processing the encounter information to generate an encounter transcript may include processing the encounter information to identify a speaker within the patient encounter. Processing the encounter information to identify a speaker within the patient encounter may include comparing the encounter information to one or more humanoid models. Processing the encounter information to generate an encounter transcript may include: processing the encounter information to associate a first potion of the encounter information with a first encounter participant; and assigning a first role to the first encounter participant. Processing the encounter information to generate an encounter transcript may include processing the encounter information to compartmentalize the encounter information into a plurality of encounter stages. At least a portion of the encounter transcript may be processed to populate at least a portion of a medical record associated with the patient encounter.

The details of one or more implementations are set forth in the accompanying drawings and the description below.

Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

System Overview

Figure 1:
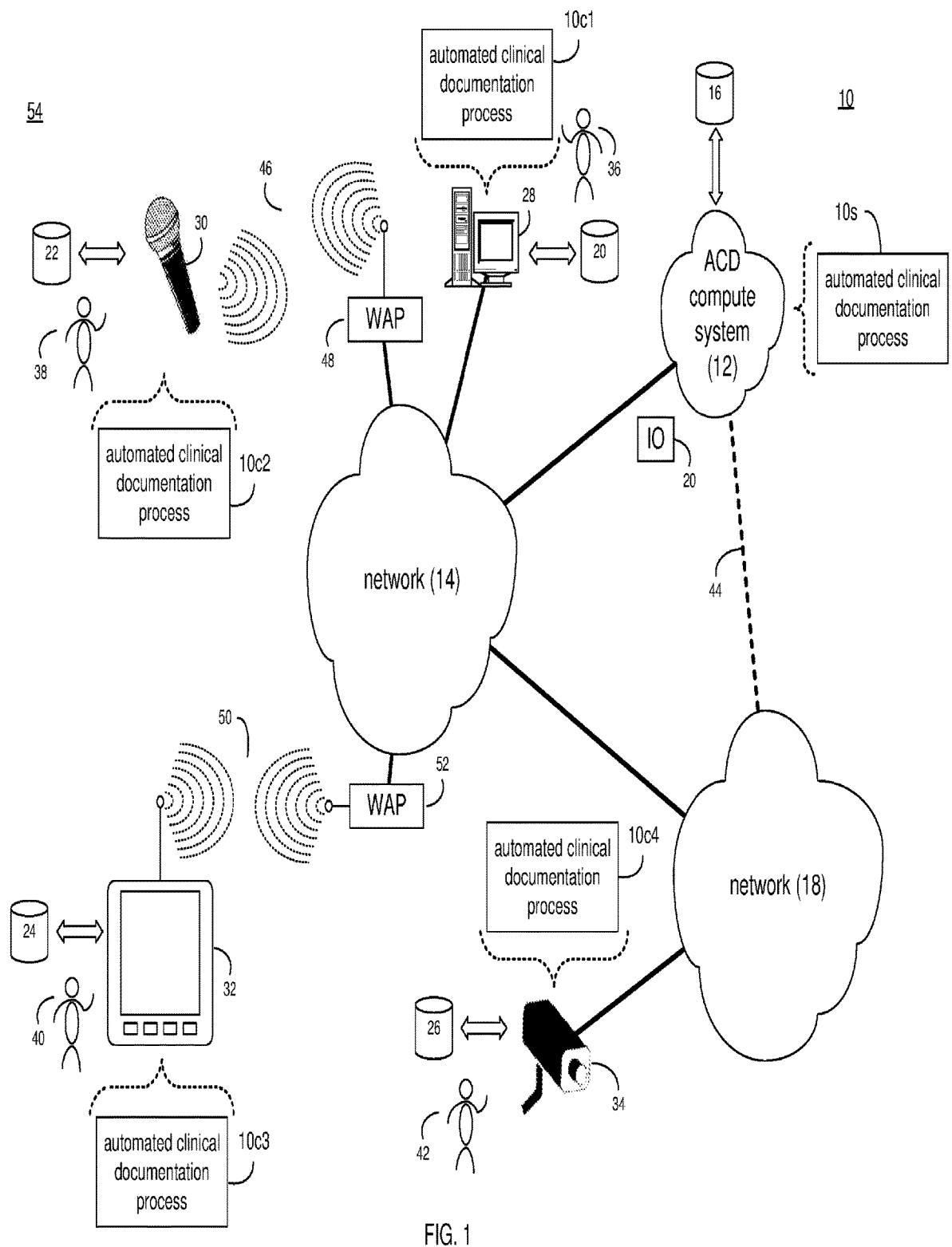
FIG. 1 is a diagrammatic view of an automated clinical documentation compute system and an automated clinical documentation process coupled to a distributed computing network.

Referring to FIG. 1, there is shown automated clinical documentation process 10. As will be discussed below in greater detail, automated clinical documentation process 10 may be configured to automate the collection and processing of clinical encounter information to generate/store/distribute medical records.

Automated clinical documentation process 10 may be implemented as a server-side process, a client-side process, or a hybrid server-side/client-side process. For example, automated clinical documentation process 10 may be implemented as a purely server-side process via automated clinical documentation process 10s. Alternatively, automated clinical documentation process 10 may be implemented as a purely client-side process via one or more of automated clinical documentation process 10c1, automated clinical documentation process 10c2, automated clinical documentation process 10c3, and automated clinical documentation process 10c4. Alternatively still, automated clinical documentation process 10 may be implemented as a hybrid server-side/client-side process via automated clinical documentation process 10s in combination with one or more of automated clinical documentation process 10c1, automated clinical documentation process 10c2, automated clinical documentation process 10c3, and automated clinical documentation process 10c4.

Accordingly, automated clinical documentation process 10 as used in this disclosure may include any combination of automated clinical documentation process 10s, automated clinical documentation process 10c1, automated clinical documentation process 10c2, automated clinical documentation process 10c3, and automated clinical documentation process 10c4.

Automated clinical documentation process 10s may be a server application and may reside on and may be executed by automated clinical documentation (ACD) compute system 12, which may be connected to network 14 (e.g., the Internet or a local area network). ACD compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of ACD compute system 12 may execute one or more operating systems, examples of which may include but are not limited to: Microsoft Windows Server™; Redhat Linux™, Unix, or a custom operating system, for example.

The instruction sets and subroutines of automated clinical documentation process 10s, which may be stored on storage device 16 coupled to ACD compute system 12, may be executed by one or more processors (not shown) and one or more memory architectures (not shown) included within ACD compute system 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Various IO requests (e.g. IO request 20) may be sent from automated clinical documentation process 10s, automated clinical documentation process 10c1, automated clinical documentation process 10c2, automated clinical documentation process 10c3 and/or automated clinical documentation process 10c4 to ACD compute system 12. Examples of IO request 20 may include but are not limited to data write requests (i.e. a request that content be written to ACD compute system 12) and data read requests (i.e. a request that content be read from ACD compute system 12).

The instruction sets and subroutines of automated clinical documentation process 10c1, automated clinical documentation process 10c2, automated clinical documentation process 10c3 and/or automated clinical documentation process 10c4, which may be stored on storage devices 20, 22, 24, 26 (respectively) coupled to ACD client electronic devices 28, 30, 32, 34 (respectively), may be executed by one or more processors (not shown) and one or more memory architectures (not shown) incorporated into ACD client electronic devices 28, 30, 32, 34 (respectively). Storage devices 20, 22, 24, 26 may include but are not limited to: hard disk drives; optical drives; RAID devices; random access memories (RAM); read-only memories (ROM), and all forms of flash memory storage devices. Examples of ACD client electronic devices 28, 30, 32, 34 may include, but are not limited to, personal computing device 28 (e.g., a smart phone, a personal digital assistant, a laptop computer, a notebook computer, and a desktop computer), audio input device 30 (e.g., a handheld microphone, a lapel microphone, an embedded microphone (such as those embedded within eyeglasses, smart phones, tablet computers and/or watches) and an audio recording device), display device 32 (e.g., a tablet computer, a computer monitor, and a smart television), machine vision input device 34 (e.g., an RGB imaging system, an infrared imaging system, an ultraviolet imaging system, a laser imaging system, a SONAR imaging system, a RADAR imaging system, and a thermal imaging system), a hybrid device (e.g., a single device that includes the functionality of one or more of the above-references devices; not shown), an audio rendering device (e.g., a speaker system, a headphone system, or an earbud system; not shown), various medical devices (e.g., medical imaging equipment, heart monitoring machines, body weight scales, body temperature thermometers, and blood pressure machines; not shown), and a dedicated network device (not shown).

Users 36, 38, 40, 42 may access ACD compute system 12 directly through network 14 or through secondary network 18. Further, ACD compute system 12 may be connected to network 14 through secondary network 18, as illustrated with link line 44.

The various ACD client electronic devices (e.g., ACD client electronic devices 28, 30, 32, 34) may be directly or indirectly coupled to network 14 (or network 18). For example, personal computing device 28 is shown directly coupled to network 14 via a hardwired network connection. Further, machine vision input device 34 is shown directly coupled to network 18 via a hardwired network connection. Audio input device 30 is shown wirelessly coupled to network 14 via wireless communication channel 46 established between audio input device 30 and wireless access point (i.e., WAP) 48, which is shown directly coupled to network 14. WAP 48 may be, for example, an IEEE 802.11a, 802.11b, 802.11g, 802.11n, Wi-Fi, and/or Bluetooth device that is capable of establishing wireless communication channel 46 between audio input device 30 and WAP 48. Display device 32 is shown wirelessly coupled to network 14 via wireless communication channel 50 established between display device 32 and WAP 52, which is shown directly coupled to network 14.

The various ACD client electronic devices (e.g., ACD client electronic devices 28, 30, 32, 34) may each execute an operating system, examples of which may include but are not limited to Microsoft Windows™, Apple Macintosh™, Redhat Linux™, or a custom operating system, wherein the combination of the various ACD client electronic devices (e.g., ACD client electronic devices 28, 30, 32, 34) and ACD compute system 12 may form modular ACD system 54.

The Automated Clinical Documentation System

Figure 2:
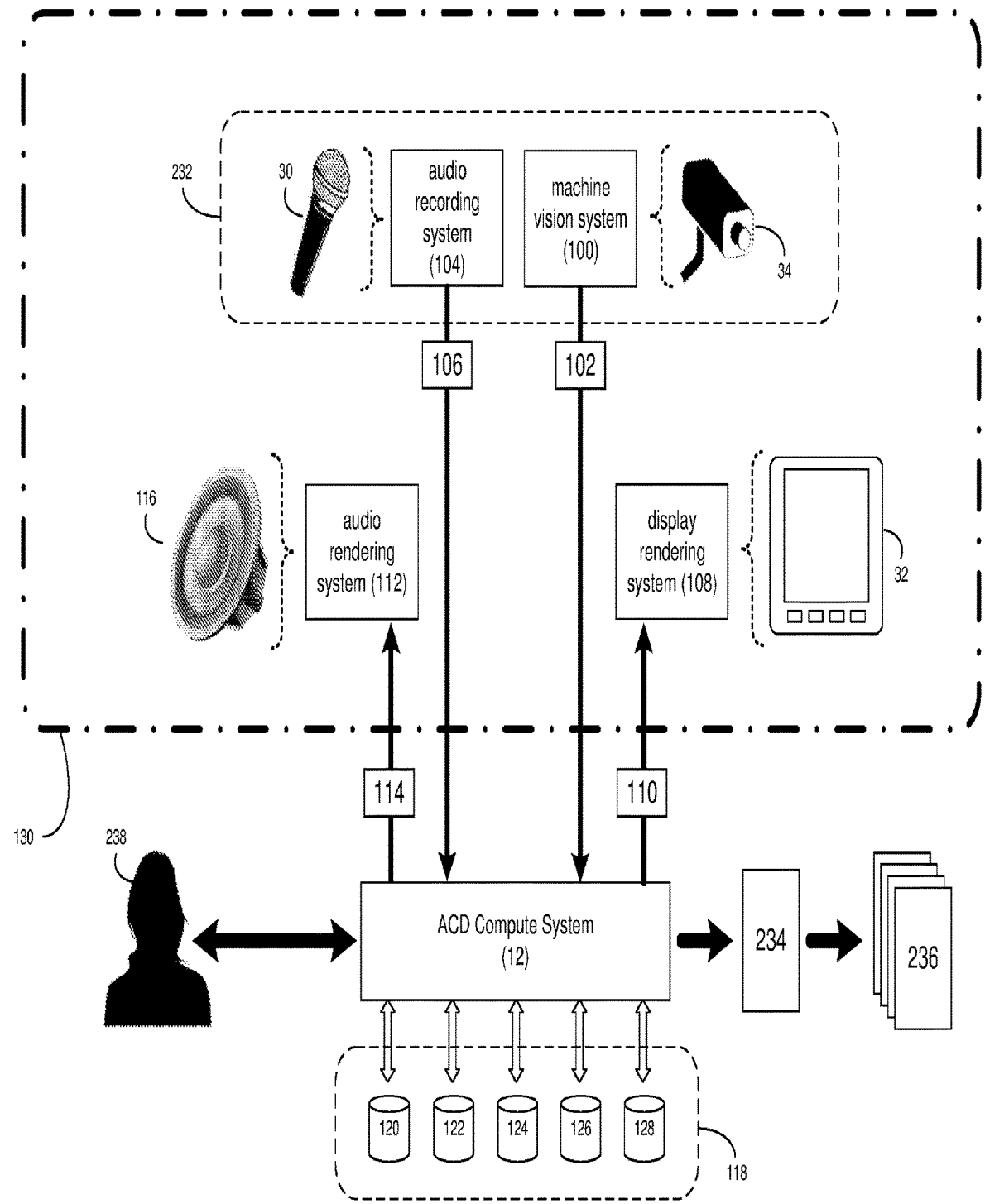
FIG. 2 is a diagrammatic view of a modular ACD system incorporating the automated clinical documentation compute system of FIG. 1.

Referring also to FIG. 2, there is shown a simplified exemplary embodiment of modular ACD system 54 that is configured to automate clinical documentation. Modular ACD system 54 may include: machine vision system 100 configured to obtain machine vision encounter information 102 concerning a patient encounter; audio recording system 104 configured to obtain audio encounter information 106 concerning the patient encounter; and a compute system (e.g., ACD compute system 12) configured to receive machine vision encounter information 102 and audio encounter information 106 from machine vision system 100 and audio recording system 104 (respectively). Modular ACD system 54 may also include: display rendering system 108 configured to render visual information 110; and audio rendering system 112 configured to render audio information 114, wherein ACD compute system 12 may be configured to provide visual information 110 and audio information 114 to display rendering system 108 and audio rendering system 112 (respectively).

Example of machine vision system 100 may include but are not limited to: one or more ACD client electronic devices (e.g., ACD client electronic device 34, examples of which may include but are not limited to an RGB imaging system, an infrared imaging system, a ultraviolet imaging system, a laser imaging system, a SONAR imaging system, a RADAR imaging system, and a thermal imaging system). Examples of audio recording system 104 may include but are not limited to: one or more ACD client electronic devices (e.g., ACD client electronic device 30, examples of which may include but are not limited to a handheld microphone (e.g., one example of a body worn microphone), a lapel microphone (e.g., another example of a body worn microphone), an embedded microphone, such as those embedded within eyeglasses, smart phones, tablet computers and/or watches (e.g., another example of a body worn microphone), and an audio recording device). Examples of display rendering system 108 may include but are not limited to: one or more ACD client electronic devices (e.g., ACD client electronic device 32, examples of which may include but are not limited to a tablet computer, a computer monitor, and a smart television). Examples of audio rendering system 112 may include but are not limited to: one or more ACD client electronic devices (e.g., audio rendering device 116, examples of which may include but are not limited to a speaker system, a headphone system, and an earbud system).

ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource. While in this particular example, five different examples of datasources 118 are shown, this is for illustrative purposes only and is not intended to be a limitation of this disclosure, as other configurations are possible and are considered to be within the scope of this disclosure.

As will be discussed below in greater detail, modular ACD system 54 may be configured to monitor a monitored space (e.g., monitored space 130) in a clinical environment, wherein examples of this clinical environment may include but are not limited to: a doctor's office, a medical facility, a medical practice, a medical lab, an urgent care facility, a medical clinic, an emergency room, an operating room, a hospital, a long term care facility, a rehabilitation facility, a nursing home, and a hospice facility. Accordingly, an example of the above-referenced patient encounter may include but is not limited to a patient visiting one or more of the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility).

Machine vision system 100 may include a plurality of discrete machine vision systems when the above-described clinical environment is larger or a higher level of resolution is desired. As discussed above, examples of machine vision system 100 may include but are not limited to: one or more ACD client electronic devices (e.g., ACD client electronic device 34, examples of which may include but are not limited to an RGB imaging system, an infrared imaging system, an ultraviolet imaging system, a laser imaging system, a SONAR imaging system, a RADAR imaging system, and a thermal imaging system). Accordingly, machine vision system 100 may include one or more of each of an RGB imaging system, an infrared imaging systems, an ultraviolet imaging systems, a laser imaging system, a SONAR imaging system, a RADAR imaging system, and a thermal imaging system.

Audio recording system 104 may include a plurality of discrete audio recording systems when the above-described clinical environment is larger or a higher level of resolution is desired. As discussed above, examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Accordingly, audio recording system 104 may include one or more of each of a handheld microphone, a lapel microphone, an embedded microphone (such as those embedded within eyeglasses, smart phones, tablet computers and/or watches) and an audio recording device.

Display rendering system 108 may include a plurality of discrete display rendering systems when the above-described clinical environment is larger or a higher level of resolution is desired. As discussed above, examples of display rendering system 108 may include but are not limited to: one or more ACD client electronic devices (e.g., ACD client electronic device 32, examples of which may include but are not limited to a tablet computer, a computer monitor, and a smart television). Accordingly, display rendering system 108 may include one or more of each of a tablet computer, a computer monitor, and a smart television.

Audio rendering system 112 may include a plurality of discrete audio rendering systems when the above-described clinical environment is larger or a higher level of resolution is desired. As discussed above, examples of audio rendering system 112 may include but are not limited to: one or more ACD client electronic devices (e.g., audio rendering device 116, examples of which may include but are not limited to a speaker system, a headphone system, or an earbud system). Accordingly, audio rendering system 112 may include one or more of each of a speaker system, a headphone system, or an earbud system.

ACD compute system 12 may include a plurality of discrete compute systems. As discussed above, ACD compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform. Accordingly, ACD compute system 12 may include one or more of each of a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

Microphone Array

Figure 3:
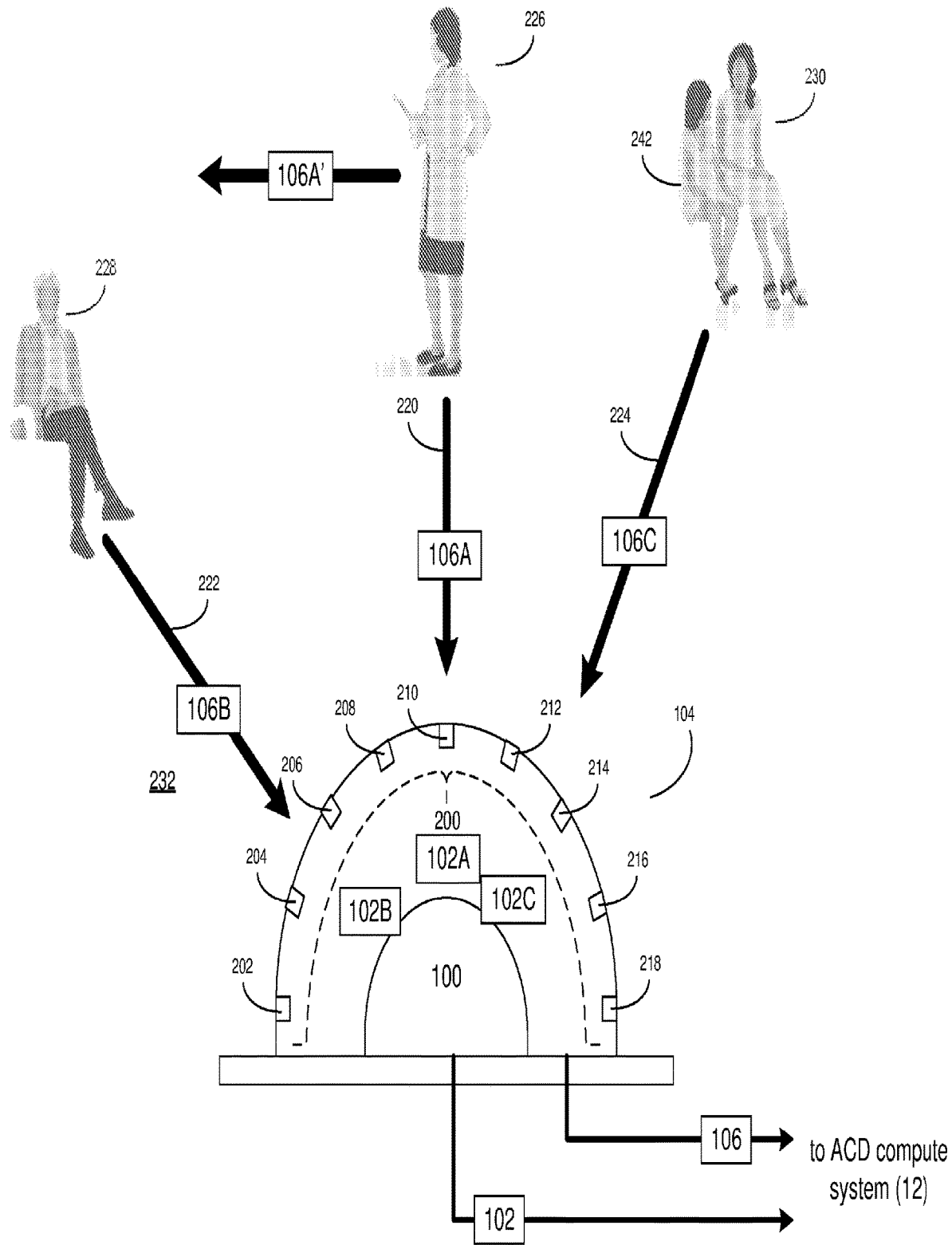
FIG. 3 is a diagrammatic view of a mixed-media ACD device included within the modular ACD system of FIG. 2.

Referring also to FIG. 3, audio recording system 104 may include microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. As will be discussed below in greater detail, modular ACD system 54 may be configured to form one or more audio recording beams (e.g., audio recording beams 220, 222, 224) via the discrete audio acquisition devices (e.g., audio acquisition devices 202, 204, 206, 208, 210, 212, 214, 216, 218) included within audio recording system 104. When forming a plurality of audio recording beams (e.g., audio recording beams 220, 222, 224), automated clinical documentation process 10 and/or modular ACD system 54 may be configured to individual and simultaneously process and steer the plurality of audio recording beams (e.g., audio recording beams 220, 222, 224).

For example, modular ACD system 54 may be further configured to steer the one or more audio recording beams (e.g., audio recording beams 220, 222, 224) toward one or more encounter participants (e.g., encounter participants 226, 228, 230) of the above-described patient encounter. Examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

Accordingly, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam. For example, modular ACD system 54 and/or audio recording system 104 may be configured to utilize various audio acquisition devices to form audio recording beam 220, thus enabling the capturing of audio (e.g., speech) produced by encounter participant 226 (as audio recording beam 220 is pointed to (i.e., directed toward) encounter participant 226). Additionally, modular ACD system 54 and/or audio recording system 104 may be configured to utilize various audio acquisition devices to form audio recording beam 222, thus enabling the capturing of audio (e.g., speech) produced by encounter participant 228 (as audio recording beam 222 is pointed to (i.e., directed toward) encounter participant 228). Additionally, modular ACD system 54 and/or audio recording system 104 may be configured to utilize various audio acquisition devices to form audio recording beam 224, thus enabling the capturing of audio (e.g., speech) produced by encounter participant 230 (as audio recording beam 224 is pointed to (i.e., directed toward) encounter participant 230). Further, modular ACD system 54 and/or audio recording system 104 may be configured to utilize null-steering processing to cancel interference between speakers and/or noise.

As is known in the art, null-steering processing is a method of spatial signal processing by which a multiple antenna transmitter or receiver may null interference signals in wireless communications, wherein null-steering processing may mitigate the impact of background noise and unknown user interference. In particular, null-steering processing may be a method of beamforming for narrowband or wideband signals that may compensate for delays of receiving signals from a specific source at different elements of an antenna array. In general and to improve performance of the antenna array, incoming signals may be summed and averaged, wherein certain signals may be weighted and compensation may be made for signal delays.

Machine vision system 100 and audio recording system 104 may be stand-alone devices (as shown in FIG. 2). Additionally/alternatively, machine vision system 100 and audio recording system 104 may be combined into one package to form mixed-media ACD device 232. For example, mixed-media ACD device 232 may be configured to be mounted to a structure (e.g., a wall, a ceiling, a beam, a column) within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility), thus allowing for easy installation of the same. Further, modular ACD system 54 may be configured to include a plurality of mixed-media ACD devices (e.g., mixed-media ACD device 232) when the above-described clinical environment is larger or a higher level of resolution is desired.

Modular ACD system 54 may be further configured to steer the one or more audio recording beams (e.g., audio recording beams 220, 222, 224) toward one or more encounter participants (e.g., encounter participants 226, 228, 230) of the patient encounter based, at least in part, upon machine vision encounter information 102. As discussed above, mixed-media ACD device 232 (and machine vision system 100/audio recording system 104 included therein) may be configured to monitor one or more encounter participants (e.g., encounter participants 226, 228, 230) of a patient encounter.

Specifically and as will be discussed below in greater detail, machine vision system 100 (either as a stand-alone system or as a component of mixed-media ACD device 232) may be configured to detect humanoid shapes within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility). And when these humanoid shapes are detected by machine vision system 100, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam (e.g., audio recording beams 220, 222, 224) that is directed toward each of the detected humanoid shapes (e.g., encounter participants 226, 228, 230).

As discussed above, ACD compute system 12 may be configured to receive machine vision encounter information 102 and audio encounter information 106 from machine vision system 100 and audio recording system 104 (respectively); and may be configured to provide visual information 110 and audio information 114 to display rendering system 108 and audio rendering system 112 (respectively). Depending upon the manner in which modular ACD system 54 (and/or mixed-media ACD device 232) is configured, ACD compute system 12 may be included within mixed-media ACD device 232 or external to mixed-media ACD device 232.

The Automated Clinical Documentation Process

As discussed above, ACD compute system 12 may execute all or a portion of automated clinical documentation process 10, wherein the instruction sets and subroutines of automated clinical documentation process 10 (which may be stored on one or more of e.g., storage devices 16, 20, 22, 24, 26) may be executed by ACD compute system 12 and/or one or more of ACD client electronic devices 28, 30, 32, 34.

Figure 4:
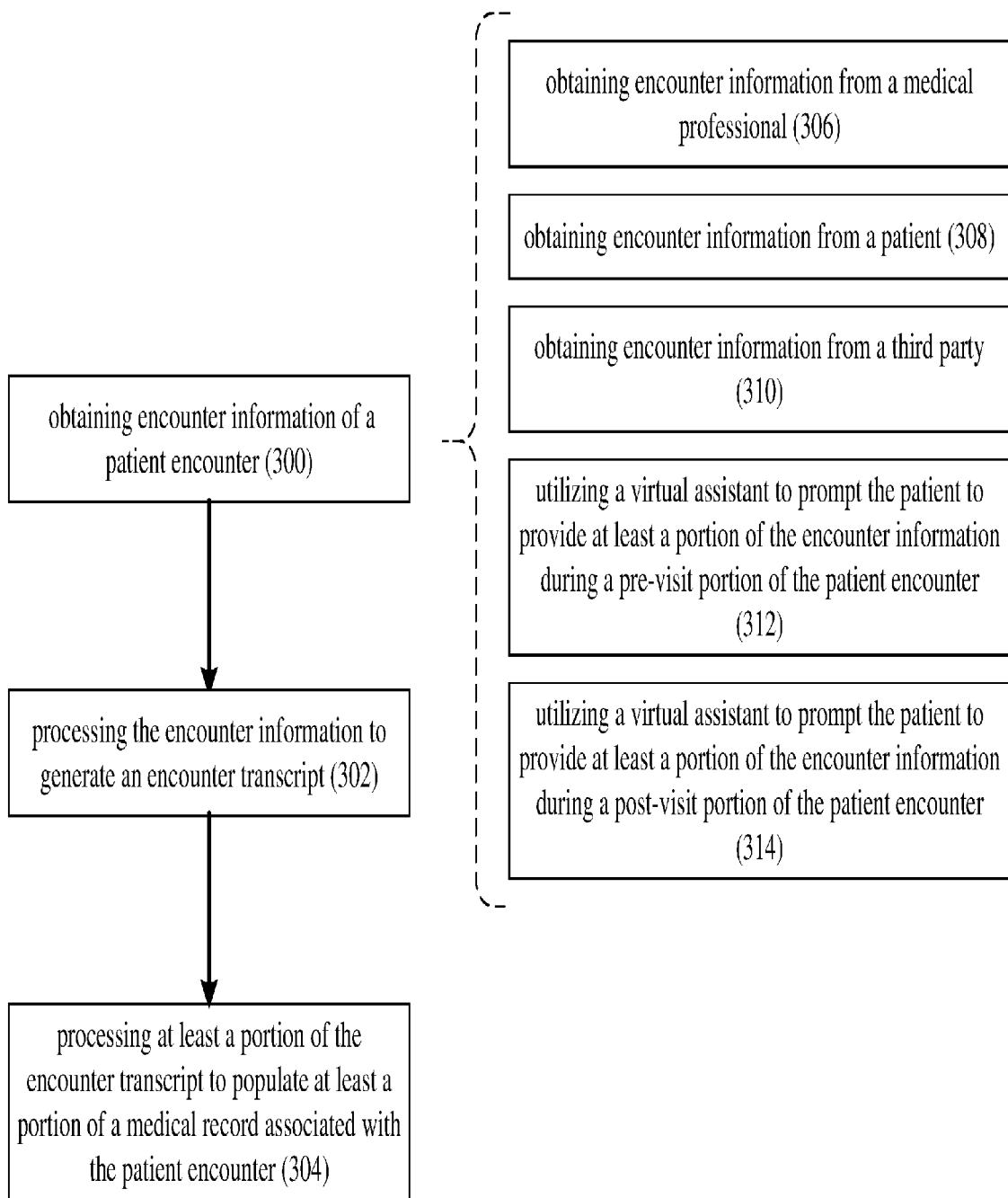
FIG. 4 is a flow chart of one implementation of the automated clinical documentation process of FIG. 1.

As discussed above, automated clinical documentation process 10 may be configured to automate the collection and processing of clinical encounter information to generate/store/distribute medical records. Accordingly and referring also to FIG. 4, automated clinical documentation process 10 may be configured to obtain 300 encounter information (e.g., machine vision encounter information 102 and/or audio encounter information 106) of a patient encounter (e.g., a visit to a doctor's office). Automated clinical documentation process 10 may further be configured to process 302 the encounter information (e.g., machine vision encounter information 102 and/or audio encounter information 106) to generate an encounter transcript (e.g., encounter transcript 234), wherein automated clinical documentation process 10 may then process 304 at least a portion of the encounter transcript (e.g., encounter transcript 234) to populate at least a portion of a medical record (e.g., medical record 236) associated with the patient encounter (e.g., the visit to the doctor's office). Encounter transcript 234 and/or medical record 236 may be reviewed by a medical professional involved with the patient encounter (e.g., a visit to a doctor's office) to determine the accuracy of the same and/or make corrections to the same.

For example, a scribe involved with (or assigned to) the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

Alternatively/additionally, a doctor involved with the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

For example, assume that a patient (e.g., encounter participant 228) visits a clinical environment (e.g., a doctor's office) because they do not feel well. They have a headache, fever, chills, a cough, and some difficulty breathing. In this particular example, a monitored space (e.g., monitored space 130) within the clinical environment (e.g., the doctor's office) may be outfitted with machine vision system 100 configured to obtain machine vision encounter information 102 concerning the patient encounter (e.g., encounter participant 228 visiting the doctor's office) and audio recording system 104 configured to obtain audio encounter information 106 concerning the patient encounter (e.g., encounter participant 228 visiting the doctor's office) via one or more audio sensors (e.g., audio acquisition devices 202, 204, 206, 208, 210, 212, 214, 216, 218).

As discussed above, machine vision system 100 may include a plurality of discrete machine vision systems if the monitored space (e.g., monitored space 130) within the clinical environment (e.g., the doctor's office) is larger or a higher level of resolution is desired, wherein examples of machine vision system 100 may include but are not limited to: an RGB imaging system, an infrared imaging system, an ultraviolet imaging system, a laser imaging system, a SONAR imaging system, a RADAR imaging system, and a thermal imaging system. Accordingly and in certain instances/embodiments, machine vision system 100 may include one or more of each of an RGB imaging system, an infrared imaging system, an ultraviolet imaging system, a laser imaging system, a SONAR imaging system, a RADAR imaging system, and a thermal imaging system positioned throughout monitored space 130, wherein each of these systems may be configured to provide data (e.g., machine vision encounter information 102) to ACD compute system 12 and/or modular ACD system 54.

As also discussed above, audio recording system 104 may include a plurality of discrete audio recording systems if the monitored space (e.g., monitored space 130) within the clinical environment (e.g., the doctor's office) is larger or a higher level of resolution is desired, wherein examples of audio recording system 104 may include but are not limited to: a handheld microphone, a lapel microphone, an embedded microphone (such as those embedded within eyeglasses, smart phones, tablet computers and/or watches) and an audio recording device. Accordingly and in certain instances/embodiments, audio recording system 104 may include one or more of each of a handheld microphone, a lapel microphone, an embedded microphone (such as those embedded within eyeglasses, smart phones, tablet computers and/or watches) and an audio recording device positioned throughout monitored space 130, wherein each of these microphones/devices may be configured to provide data (e.g., audio encounter information 106) to ACD compute system 12 and/or modular ACD system 54.

Since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and via machine vision encounter information 102, visual speech recognition (via visual lip reading functionality) may be utilized by automated clinical documentation process 10 to further effectuate the gathering of audio encounter information 106.

Accordingly and when obtaining 300 encounter information (e.g., machine vision encounter information 102 and/or audio encounter information 106), automated clinical documentation process 10 may: obtain 306 encounter information (e.g., machine vision encounter information 102 and/or audio encounter information 106) from a medical professional (e.g., encounter participant 226); obtain 308 encounter information (e.g., machine vision encounter information 102 and/or audio encounter information 106) from a patient (e.g., encounter participant 228); and/or obtain 310 encounter information (e.g., machine vision encounter information 102 and/or audio encounter information 106) from a third party (e.g., encounter participant 230). Further and when obtaining 300 encounter information (e.g., machine vision encounter information 102 and/or audio encounter information 106), automated clinical documentation process 10 may obtain 300 the encounter information (e.g., machine vision encounter information 102 and/or audio encounter information 106) from previous (related or unrelated) patient encounters. For example, if the current patient encounter is actually the third visit that the patient is making concerning e.g., shortness of breath, the encounter information from the previous two visits (i.e., the previous two patient encounters) may be highly-related and may be obtained 300 by automated clinical documentation process 10.

When automated clinical documentation process 10 obtains 300 the encounter information, automated clinical documentation process 10 may utilize 312 a virtual assistant (e.g., virtual assistant 238) to prompt the patient (e.g., encounter participant 228) to provide at least a portion of the encounter information (e.g., machine vision encounter information 102 and/or audio encounter information 106) during a pre-visit portion (e.g., a patient intake portion) of the patient encounter (e.g., encounter participant 228 visiting the doctor's office).

Further and when automated clinical documentation process 10 obtains 300 encounter information, automated clinical documentation process 10 may utilize 314 a virtual assistant (e.g., virtual assistant 238) to prompt the patient (e.g., encounter participant 228) to provide at least a portion of the encounter information (e.g., machine vision encounter information 102 and/or audio encounter information 106) during a post-visit portion (e.g., a patient follow-up portion) of the patient encounter (e.g., encounter participant 228 visiting the doctor's office).

Automated Transcript Generation

Automated clinical documentation process 10 may be configured to process the encounter information (e.g., machine vision encounter information 102 and/or audio encounter information 106) to generate encounter transcript 234 that may be automatically formatted and punctuated.

Figure 5:
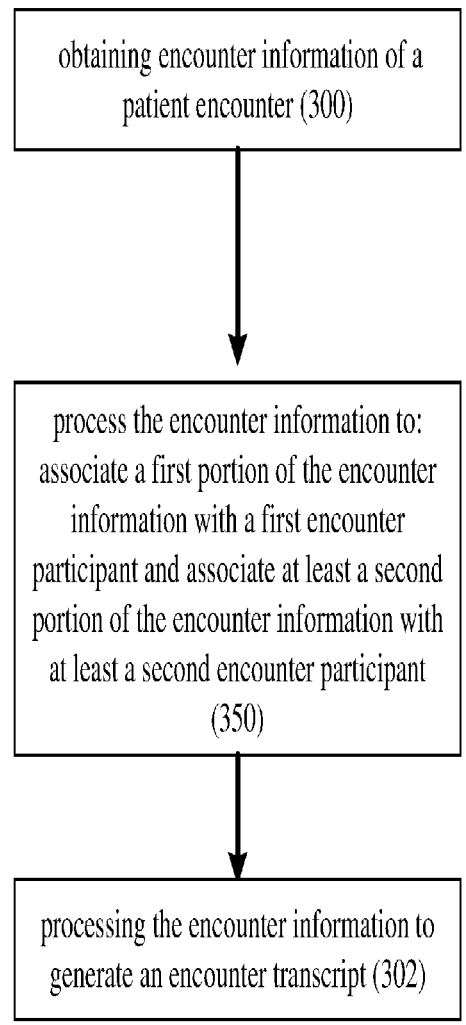
FIG. 5 is a flow chart of another implementation of the automated clinical documentation process of FIG. 1.

Accordingly and referring also to FIG. 5, automated clinical documentation process 10 may be configured to obtain 300 encounter information (e.g., machine vision encounter information 102 and/or audio encounter information 106) of a patient encounter (e.g., a visit to a doctor's office).

Automated clinical documentation process 10 may process 350 the encounter information (e.g., machine vision encounter information 102 and/or audio encounter information 106) to: associate a first portion of the encounter information (e.g., machine vision encounter information 102 and/or audio encounter information 106) with a first encounter participant, and associate at least a second portion of the encounter information (e.g., machine vision encounter information 102 and/or audio encounter information 106) with at least a second encounter participant.

As discussed above, modular ACD system 54 may be configured to form one or more audio recording beams (e.g., audio recording beams 220, 222, 224) via the discrete audio acquisition devices (e.g., discrete audio acquisition devices 202, 204, 206, 208, 210, 212, 214, 216, 218) included within audio recording system 104, wherein modular ACD system 54 may be further configured to steer the one or more audio recording beams (e.g., audio recording beams 220, 222, 224) toward one or more encounter participants (e.g., encounter participants 226, 228, 230) of the above-described patient encounter.

Accordingly and continuing with the above-stated example, modular ACD system 54 may steer audio recording beam 220 toward encounter participant 226, may steer audio recording beam 222 toward encounter participant 228, and may steer audio recording beam 224 toward encounter participant 230. Accordingly and due to the directionality of audio recording beams 220, 222, 224, audio encounter information 106 may include three components, namely audio encounter information 106A (which is obtained via audio recording beam 220), audio encounter information 106B (which is obtained via audio recording beam 222) and audio encounter information 106C (which is obtained via audio recording beam 220).

Further and as discussed above, ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

Accordingly, automated clinical documentation process 10 may process 350 the encounter information (e.g., machine vision encounter information 102 and/or audio encounter information 106) to: associate a first portion (e.g., encounter information 106A) of the encounter information (e.g., audio encounter information 106) with a first encounter participant (e.g., encounter participant 226), and associate at least a second portion (e.g., encounter information 106B, 106C) of the encounter information (e.g., audio encounter information 106) with at least a second encounter participant (e.g., encounter participants 228, 230; respectively).

Further and when processing 350 the encounter information (e.g., audio encounter information 106A, 106B, 106C), automated clinical documentation process 10 may compare each of audio encounter information 106A, 106B, 106C to the voice prints defined within the above-referenced voice print datasource so that the identity of encounter participants 226, 228, 230 (respectively) may be determined. Accordingly, if the voice print datasource includes a voice print that corresponds to one or more of the voice of encounter participant 226 (as heard within audio encounter information 106A), the voice of encounter participant 228 (as heard within audio encounter information 106B) or the voice of encounter participant 230 (as heard within audio encounter information 106C), the identity of one or more of encounter participants 226, 228, 230 may be defined. And in the event that a voice heard within one or more of audio encounter information 106A, audio encounter information 106B or audio encounter information 106C is unidentifiable, that one or more particular encounter participant may be defined as "Unknown Participant".

Once the voices of encounter participants 226, 228, 230 are processed 350, automated clinical documentation process 10 may generate 302 an encounter transcript (e.g., encounter transcript 234) based, at least in part, upon the first portion of the encounter information (e.g., audio encounter information 106A) and the at least a second portion of the encounter information (e.g., audio encounter information 106B. 106C).

Automated Role Assignment

Automated clinical documentation process 10 may be configured to automatically define roles for the encounter participants (e.g., encounter participants 226, 228, 230) in the patient encounter (e.g., a visit to a doctor's office)

Figure 6:
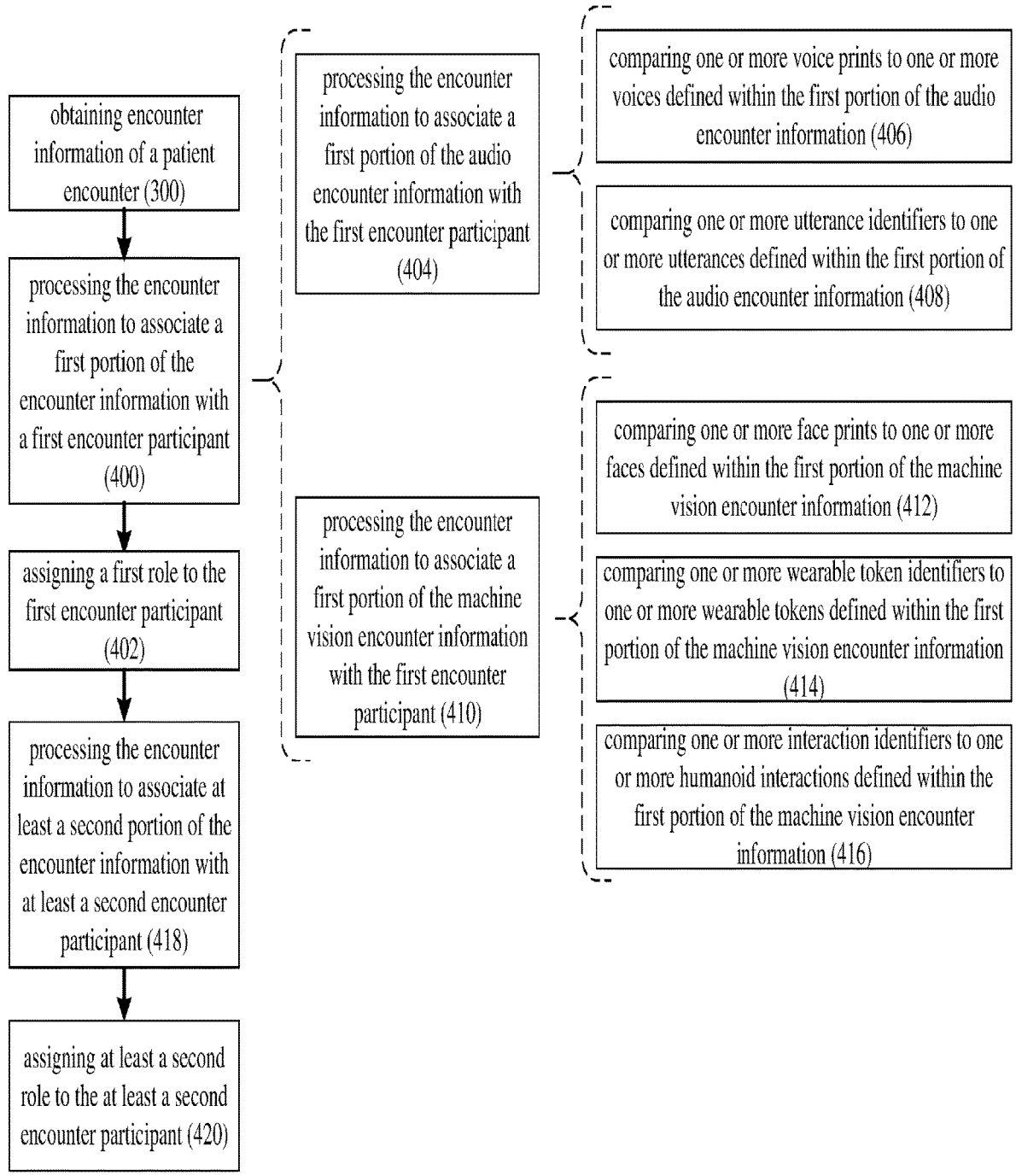
FIG. 6 is a flow chart of another implementation of the automated clinical documentation process of FIG. 1.

Accordingly and referring also to FIG. 6, automated clinical documentation process 10 may be configured to obtain 300 encounter information (e.g., machine vision encounter information 102 and/or audio encounter information 106) of a patient encounter (e.g., a visit to a doctor's office).

Automated clinical documentation process 10 may then process 400 the encounter information (e.g., machine vision encounter information 102 and/or audio encounter information 106) to associate a first portion of the encounter information with a first encounter participant (e.g., encounter participant 226) and assign 402 a first role to the first encounter participant (e.g., encounter participant 226).

When processing 400 the encounter information (e.g., machine vision encounter information 102 and/or audio encounter information 106) to associate the first portion of the encounter information with the first encounter participant (e.g., encounter participant 226), automated clinical documentation process 10 may process 404 the encounter information (e.g., machine vision encounter information 102 and/or audio encounter information 106) to associate a first portion of the audio encounter information (e.g., audio encounter information 106A) with the first encounter participant (e.g., encounter participant 226).

Specifically and when processing 404 the encounter information (e.g., machine vision encounter information 102 and/or audio encounter information 106) to associate the first portion of the audio encounter information (e.g., audio encounter information 106A) with the first encounter participant (e.g., encounter participant 226), automated clinical documentation process 10 may compare 406 one or more voice prints (defined within voice print datasource) to one or more voices defined within the first portion of the audio encounter information (e.g., audio encounter information 106A); and may compare 408 one or more utterance identifiers (defined within utterance datasource) to one or more utterances defined within the first portion of the audio encounter information (e.g., audio encounter information 106A); wherein comparisons 406, 408 may allow automated clinical documentation process 10 to assign 402 a first role to the first encounter participant (e.g., encounter participant 226). For example, if the identity of encounter participant 226 can be defined via voice prints, a role for encounter participant 226 may be assigned 402 if that identity defined is associated with a role (e.g., the identity defined for encounter participant 226 is Doctor Susan Jones). Further, if an utterance made by encounter participant 226 is "I am Doctor Susan Jones", this utterance may allow a role for encounter participant 226 to be assigned 402.

When processing 400 the encounter information (e.g., machine vision encounter information 102 and/or audio encounter information 106) to associate the first portion of the encounter information with the first encounter participant (e.g., encounter participant 226), automated clinical documentation process 10 may process 410 the encounter information (e.g., machine vision encounter information 102 and/or audio encounter information 106) to associate a first portion of the machine vision encounter information (e.g., machine vision encounter information 102A) with the first encounter participant (e.g., encounter participant 226).

Specifically and when processing 410 the encounter information (e.g., machine vision encounter information 102 and/or audio encounter information 106) to associate the first portion of the machine vision encounter information (e.g., machine vision encounter information 102A) with the first encounter participant (e.g., encounter participant 226), automated clinical documentation process 10 may compare 412 one or more face prints (defined within face print datasource) to one or more faces defined within the first portion of the machine vision encounter information (e.g., machine vision encounter information 102A); compare 414 one or more wearable token identifiers (defined within wearable token identifier datasource) to one or more wearable tokens defined within the first portion of the machine vision encounter information (e.g., machine vision encounter information 102A); and compare 416 one or more interaction identifiers (defined within interaction identifier datasource) to one or more humanoid interactions defined within the first portion of the machine vision encounter information (e.g., machine vision encounter information 102A); wherein comparisons 412, 414, 416 may allow automated clinical documentation process 10 to assign 402 a first role to the first encounter participant (e.g., encounter participant 226). For example, if the identity of encounter participant 226 can be defined via face prints, a role for encounter participant 226 may be assigned 402 if that identity defined is associated with a role (e.g., the identity defined for encounter participant 226 is Doctor Susan Jones). Further, if a wearable token worn by encounter participant 226 can be identified as a wearable token assigned to Doctor Susan Jones, a role for encounter participant 226 may be assigned 402. Additionally, if an interaction made by encounter participant 226 corresponds to the type of interaction that is made by a doctor, the existence of this interaction may allow a role for encounter participant 226 to be assigned 402.

Examples of such wearable tokens may include but are not limited to wearable devices that may be worn by the medical professionals when they are within monitored space 130 (or after they leave monitored space 130). For example, these wearable tokens may be worn by medical professionals when e.g., they are moving between monitored rooms within monitored space 130, travelling to and/or from monitored space 130, and/or outside of monitored space 130 (e.g., at home).

Additionally, automated clinical documentation process 10 may process 418 the encounter information (e.g., machine vision encounter information 102 and/or audio encounter information 106) to associate at least a second portion of the encounter information with at least a second encounter participant; and may assign 420 at least a second role to the at least a second encounter participant.

Specifically, automated clinical documentation process 10 may process 418 the encounter information (e.g., machine vision encounter information 102 and/or audio encounter information 106) to associate at least a second portion of the encounter information with at least a second encounter participant. For example, automated clinical documentation process 10 may process 418 the encounter information (e.g., machine vision encounter information 102 and/or audio encounter information 106) to associate audio encounter information 106B and machine vision encounter information 102B with encounter participant 228 and may associate audio encounter information 106C and machine vision encounter information 102C with encounter participant 230.

Further, automated clinical documentation process 10 may assign 420 at least a second role to the at least a second encounter participant. For example, automated clinical documentation process 10 may assign 420 a role to encounter participants 228, 230.

Automated Movement Tracking

Automated clinical documentation process 10 may be configured to track the movement and/or interaction of humanoid shapes within the monitored space (e.g., monitored space 130) during the patient encounter (e.g., a visit to a doctor's office) so that e.g., the automated clinical documentation process 10 knows when encounter participants (e.g., one or more of encounter participants 226, 228, 230) enter, exit or cross paths within monitored space 130.

Figure 7:
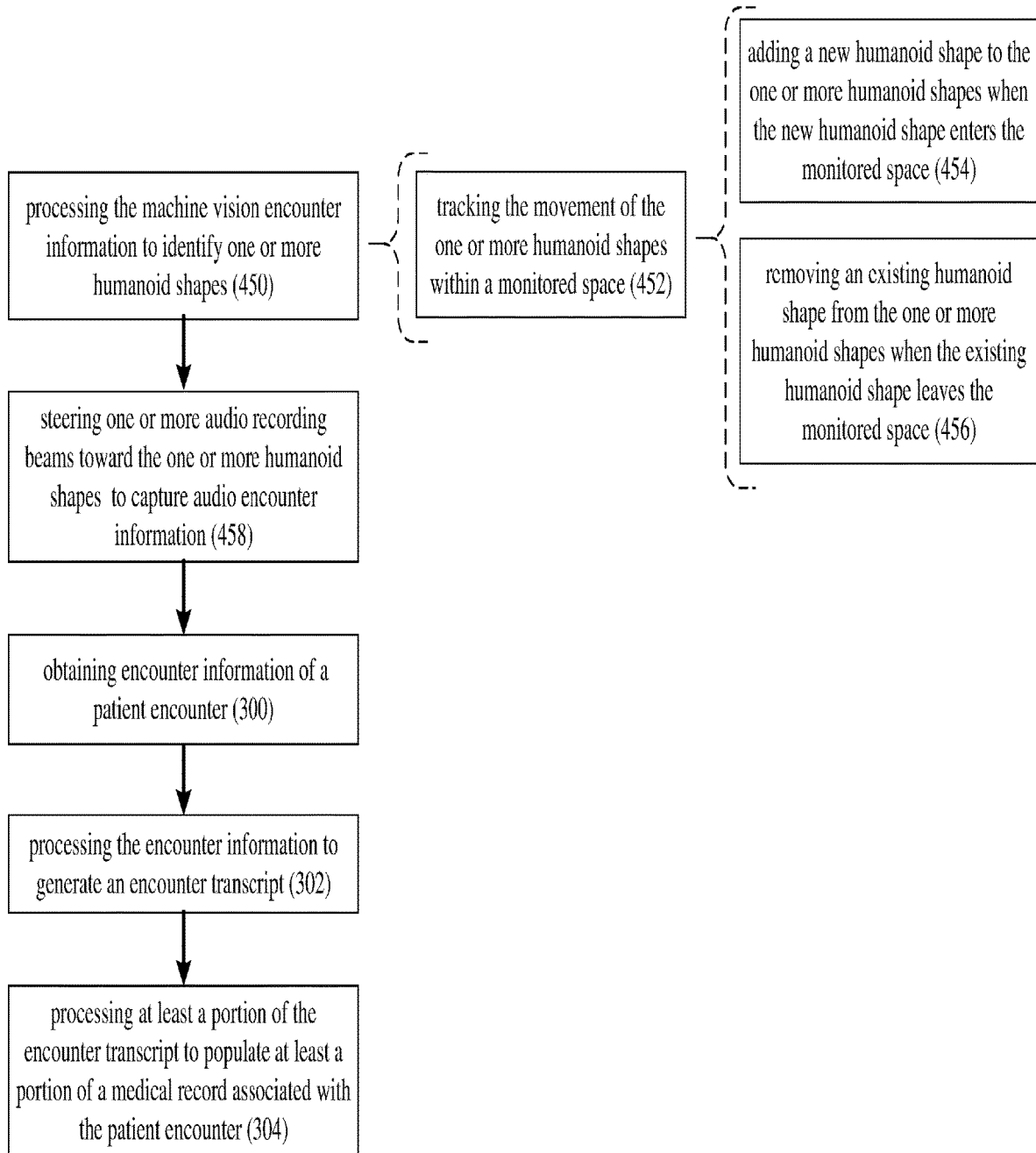
FIG. 7 is a flow chart of another implementation of the automated clinical documentation process of FIG. 1.

Accordingly and referring also to FIG. 7, automated clinical documentation process 10 may process 450 the machine vision encounter information (e.g., machine vision encounter information 102) to identify one or more humanoid shapes. As discussed above, examples of machine vision system 100 generally (and ACD client electronic device 34 specifically) may include but are not limited to one or more of an RGB imaging system, an infrared imaging system, an ultraviolet imaging system, a laser imaging system, a SONAR imaging system, a RADAR imaging system, and a thermal imaging system).

When ACD client electronic device 34 includes a visible light imaging system (e.g., an RGB imaging system), ACD client electronic device 34 may be configured to monitor various objects within monitored space 130 by recording motion video in the visible light spectrum of these various objects. When ACD client electronic device 34 includes an invisible light imaging systems (e.g., a laser imaging system, an infrared imaging system and/or an ultraviolet imaging system), ACD client electronic device 34 may be configured to monitor various objects within monitored space 130 by recording motion video in the invisible light spectrum of these various objects. When ACD client electronic device 34 includes an X-ray imaging system, ACD client electronic device 34 may be configured to monitor various objects within monitored space 130 by recording energy in the X-ray spectrum of these various objects. When ACD client electronic device 34 includes a SONAR imaging system, ACD client electronic device 34 may be configured to monitor various objects within monitored space 130 by transmitting soundwaves that may be reflected off of these various objects. When ACD client electronic device 34 includes a RADAR imaging system, ACD client electronic device 34 may be configured to monitor various objects within monitored space 130 by transmitting radio waves that may be reflected off of these various objects. When ACD client electronic device 34 includes a thermal imaging system, ACD client electronic device 34 may be configured to monitor various objects within monitored space 130 by tracking the thermal energy of these various objects.

As discussed above, ACD compute system 12 may be configured to access one or more datasources 118 (e.g., plurality of individual datasources 120, 122, 124, 126, 128), wherein examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

Accordingly and when processing 450 the machine vision encounter information (e.g., machine vision encounter information 102) to identify one or more humanoid shapes, automated clinical documentation process 10 may be configured to compare the humanoid shapes defined within one or more datasources 118 to potential humanoid shapes within the machine vision encounter information (e.g., machine vision encounter information 102).

When processing 450 the machine vision encounter information (e.g., machine vision encounter information 102) to identify one or more humanoid shapes, automated clinical documentation process 10 may track 452 the movement of the one or more humanoid shapes within the monitored space (e.g., monitored space 130). For example and when tracking 452 the movement of the one or more humanoid shapes within monitored space 130, automated clinical documentation process 10 may add 454 a new humanoid shape to the one or more humanoid shapes when the new humanoid shape enters the monitored space (e.g., monitored space 130) and/or may remove 456 an existing humanoid shape from the one or more humanoid shapes when the existing humanoid shape leaves the monitored space (e.g., monitored space 130).

For example, assume that a lab technician (e.g., encounter participant 242) temporarily enters monitored space 130 to chat with encounter participant 230. Accordingly, automated clinical documentation process 10 may add 454 encounter participant 242 to the one or more humanoid shapes being tracked 452 when the new humanoid shape (i.e., encounter participant 242) enters monitored space 130. Further, assume that the lab technician (e.g., encounter participant 242) leaves monitored space 130 after chatting with encounter participant 230. Therefore, automated clinical documentation process 10 may remove 456 encounter participant 242 from the one or more humanoid shapes being tracked 452 when the humanoid shape (i.e., encounter participant 242) leaves monitored space 130.

Also and when tracking 452 the movement of the one or more humanoid shapes within monitored space 130, automated clinical documentation process 10 may monitor the trajectories of the various humanoid shapes within monitored space 130. Accordingly, assume that when leaving monitored space 130, encounter participant 242 walks in front of (or behind) encounter participant 226. As automated clinical documentation process 10 is monitoring the trajectories of (in this example) encounter participant 242 (who is e.g., moving from left to right) and encounter participant 226 (who is e.g., stationary), when encounter participant 242 passes in front of (or behind) encounter participant 226, the identities of these two humanoid shapes may not be confused by automated clinical documentation process 10.

Automated clinical documentation process 10 may be configured to obtain 300 the encounter information of the patient encounter (e.g., a visit to a doctor's office), which may include machine vision encounter information 102 (in the manner described above) and/or audio encounter information 106.

Automated clinical documentation process 10 may steer 458 one or more audio recording beams (e.g., audio recording beams 220, 222, 224) toward the one or more humanoid shapes (e.g., encounter participants 226, 228, 230) to capture audio encounter information (e.g., audio encounter information 106), wherein audio encounter information 106 may be included within the encounter information (e.g., machine vision encounter information 102 and/or audio encounter information 106).

Specifically and as discussed above, automated clinical documentation process 10 (via modular ACD system 54 and/or audio recording system 104) may utilize one or more of the discrete audio acquisition devices (e.g., audio acquisition devices 202, 204, 206, 208, 210, 212, 214, 216, 218) to form an audio recording beam. For example, modular ACD system 54 and/or audio recording system 104 may be configured to utilize various audio acquisition devices to form audio recording beam 220, thus enabling the capturing of audio (e.g., speech) produced by encounter participant 226 (as audio recording beam 220 is pointed to (i.e., directed toward) encounter participant 226). Additionally, modular ACD system 54 and/or audio recording system 104 may be configured to utilize various audio acquisition devices to form audio recording beam 222, thus enabling the capturing of audio (e.g., speech) produced by encounter participant 228 (as audio recording beam 222 is pointed to (i.e., directed toward) encounter participant 228). Additionally, modular ACD system 54 and/or audio recording system 104 may be configured to utilize various audio acquisition devices to form audio recording beam 224, thus enabling the capturing of audio (e.g., speech) produced by encounter participant 230 (as audio recording beam 224 is pointed to (i.e., directed toward) encounter participant 230).

Once obtained, automated clinical documentation process 10 may process 302 the encounter information (e.g., machine vision encounter information 102 and/or audio encounter information 106) to generate encounter transcript 234 and may process 304 at least a portion of encounter transcript 234 to populate at least a portion of a medical record (e.g., medical record 236) associated with the patient encounter (e.g., a visit to a doctor's office).

Figure 8:
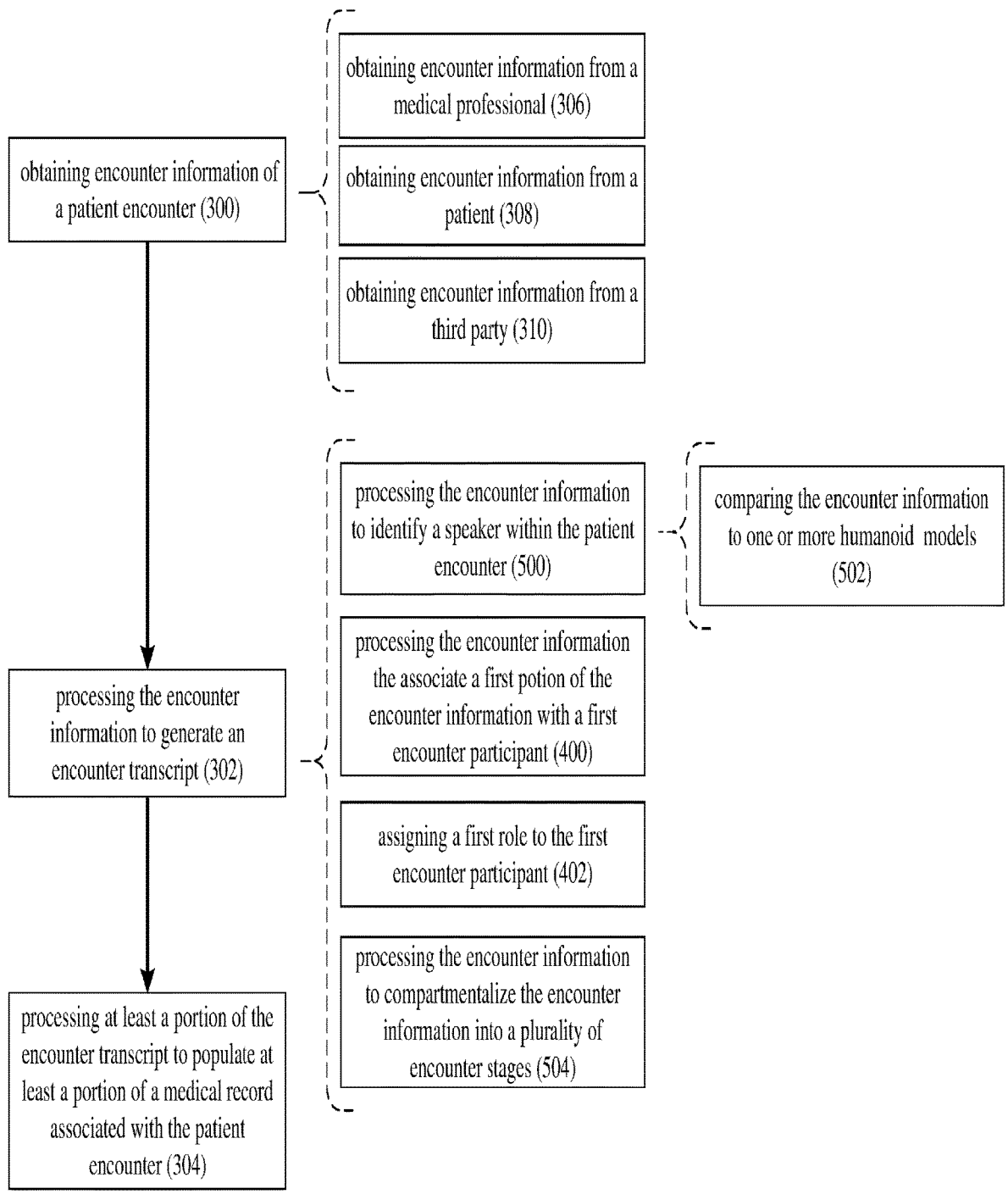
FIG. 8 is a flow chart of another implementation of the automated clinical documentation process of FIG. 1.

Video-Enhanced Speaker Identification:

Automated clinical documentation process 10 may be configured to perform video-enhanced speaker identification within monitored space 130. Accordingly and referring also to FIG. 8, automated clinical documentation process 10 may be configured to obtain 300 encounter information of a patient encounter (e.g., a visit to a doctor's office), wherein (and as discussed above) this encounter information may include machine vision encounter information 102 and/or audio encounter information 106.

As discussed above and when obtaining 300 encounter information (e.g., machine vision encounter information 102 and/or audio encounter information 106), automated clinical documentation process 10 may: obtain 306 encounter information (e.g., machine vision encounter information 102 and/or audio encounter information 106) from a medical professional (e.g., encounter participant 226); obtain 308 encounter information (e.g., machine vision encounter information 102 and/or audio encounter information 106) from a patient (e.g., encounter participant 228); and/or obtain 310 encounter information (e.g., machine vision encounter information 102 and/or audio encounter information 106) from a third party (e.g., encounter participant 230).

Further and as discussed above, automated clinical documentation process 10 may be configured to process 302 the encounter information (e.g., machine vision encounter information 102 and/or audio encounter information 106) to generate an encounter transcript (e.g., encounter transcript 234). Once the encounter transcript (e.g., encounter transcript 234) is generated, automated clinical documentation process 10 may process 304 at least a portion of the encounter transcript (e.g., encounter transcript 234) to populate at least a portion of a medical record (e.g., medical record 236) associated with the patient encounter (e.g., the visit to the doctor's office). As discussed above, encounter transcript 234 and/or medical record 236 may be reviewed by a medical professional involved with the patient encounter (e.g., a visit to a doctor's office) to determine the accuracy of the same and/or make corrections to the same.

For example, a scribe involved with (or assigned to) the patient encounter (e.g., a visit to a doctor's office) and/or a doctor involved with the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

When processing 302 the encounter information (e.g., machine vision encounter information 102 and/or audio encounter information 106) to generate an encounter transcript (e.g., encounter transcript 234), automated clinical documentation process 10 may process 500 the encounter information (e.g., machine vision encounter information 102 and/or audio encounter information 106) to identify a speaker within the patient encounter (e.g., a visit to a doctor's office).

For example and during the patient encounter (e.g., a visit to a doctor's office), many participants may be involved. As discussed with respect to the above-described patient encounter (e.g., a visit to a doctor's office), encounter participants 226, 228, 230, 242 may be involved. And during such a patient encounter (e.g., a visit to a doctor's office), one or more of encounter participants 226, 228, 230, 242 may be speaking, while one or more of encounter participants 226, 228, 230, 242 may be listening. Accordingly, automated clinical documentation process 10 may be configured to process 500 the encounter information (e.g., machine vision encounter information 102 and/or audio encounter information 106) to identify which (if any) of encounter participants 226, 228, 230, 242 are speaking.

When processing 500 the encounter information (e.g., machine vision encounter information 102 and/or audio encounter information 106) to identify a speaker within the patient encounter (e.g., a visit to a doctor's office), automated clinical documentation process 10 may compare 502 the encounter information (e.g., machine vision encounter information 102 and/or audio encounter information 106) to one or more humanoid models.

As discussed above, automated clinical documentation process 10 may process the machine vision encounter information (e.g., machine vision encounter information 102) to identify one or more potential humanoid shapes included within machine vision encounter information 102. These identified potential humanoid shapes may then be compared to humanoid shapes defined within one or more datasources 118. The humanoid shapes defined within one or more datasources 118 may be defined with one or more humanoid models generated using e.g., various known machine learning techniques. For example, video-based data of participants within numerous patient encounters may be processed by such a machine learning process so that such humanoid models may be defined.

These humanoid models may define e.g., a humanoid model of a person that is speaking and a humanoid model of a person that is listening. For example, automated clinical documentation process 10 may define the following:

Speaking Humanoid Model: a humanoid shape that includes a moving mouth, moving lips, a moving head, moving hands, and/or a higher level of mobility; and Listening Humanoid Model: a humanoid shape that includes a non-moving mouth, non-moving lips, a non-moving head, non-moving hands, and/or a lower level of mobility.

Accordingly, automated clinical documentation process 10 may process machine vision encounter information 102 to identify one or more potential humanoid shapes included within machine vision encounter information 102 and may compare 502 the one or more potential humanoid shapes included within machine vision encounter information 102 to (in this example) the above-described Speaking Humanoid Model and the above-described Listening Humanoid Model to identify the speakers within the patient encounter (e.g., a visit to a doctor's office).

Once the speaker(s) and/or the listener(s) are identified by automated clinical documentation process 10, automated clinical documentation process 10 may steer one or more audio recording beams (e.g., audio recording beams 220, 222, 224) toward the speaker(s) and/or the listener(s) (e.g., encounter participants 226, 228, 230, 242) to capture audio encounter information (e.g., audio encounter information 106). As discussed above, automated clinical documentation process 10 (via modular ACD system 54 and/or audio recording system 104) may utilize one or more of the discrete audio acquisition devices (e.g., audio acquisition devices 202, 204, 206, 208, 210, 212, 214, 216, 218) to form these audio recording beams.

When processing 302 the encounter information (e.g., machine vision encounter information 102 and/or audio encounter information 106) to generate an encounter transcript (e.g., encounter transcript 234), automated clinical documentation process 10 may process 400 the encounter information (e.g., machine vision encounter information 102 and/or audio encounter information 106) to associate a first potion of the encounter information (e.g., machine vision encounter information 102 and/or audio encounter information 106) with a first encounter participant and may assign 402 a first role to the first encounter participant.

Specifically and by examining the encounter information (e.g., machine vision encounter information 102 and/or audio encounter information 106), automated clinical documentation process 10 may determine the roles (e.g., patient, doctor, third party) of the encounter participants (e.g., encounter participants 226, 228, 230, 242).

For example and when assigning 402 a first role to the first encounter participant (e.g., encounter participants 226, 228, 230, 242), automated clinical documentation process 10 may examine the encounter information (e.g., machine vision encounter information 102 and/or audio encounter information 106) to e.g., determine:

if the participant is sitting on an examination table, which may be indicative of the participant being a patient;

if the participant is sitting in a patient chair, which may be indicative of the participant being a patient;

if the participant entered the examination room first, which may be indicative of the participant being a patient;

if the participant moved from the patient's chair to the examination table, which may be indicative of the participant being a patient;

if the participant is in one or more "patient zones" (e.g., the patient chair, the examination table), which may be indicative of the participant being a patient;

if the participant has a lower level of movement within the examination room, which may be indicative of the participant being a patient;

if the participant is dressed like a "patient" (e.g., wearing an examination robe), which may be indicative of the participant being a patient;

if the participant is performing "patient tasks" (e.g., being examined with a stethoscope, and having blood pressure readings taken), which may be indicative of the participant being a doctor;

if the participant is sitting behind a desk, which may be indicative of the participant being a doctor;

if the participant is standing, which may be indicative of the participant being a doctor;

if the participant has a higher level of movement within the examination room, which may be indicative of the participant being a doctor;

if the participant is in one or more "doctor zones" (e.g., behind a desk), which may be indicative of the participant being a doctor;

if the participant is performing "doctor tasks" (e.g., examining someone with a stethoscope, and taking blood pressure readings), which may be indicative of the participant being a doctor; and if the participant is dressed like a "medical professional" (e.g., wearing a smock), which may be indicative of the participant being a doctor.

In addition to the visual indicators defined above, automated clinical documentation process 10 may utilize other information to assign 402 a first role to the first encounter participant (e.g., encounter participants 226, 228, 230, 242).

As discussed above, ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

Accordingly, one or more datasources 118 may define a face print for the medical professionals working at the medical facility. Therefore, automated clinical documentation process 10 utilize such a face print to assign 402 a first role to the first encounter participant (e.g., encounter participants 226, 228, 230, 242). Accordingly, if the face of a participant (e.g., encounter participant 226) defined within machine vision encounter information 102 matches a face print of a Dr. Smith that works at the clinical environment, the role assigned 402 to encounter participant 226 by automated clinical documentation process 10 may be "doctor".

Further, one or more datasources 118 may define a voiceprint for the medical professionals working at the clinical environment. Therefore, automated clinical documentation process 10 utilize such voiceprints to assign 402 a first role to the first encounter participant (e.g., encounter participants 226, 228, 230, 242). Accordingly, if the voice of a participant (e.g., encounter participant 226) defined within audio encounter information 106 matches a voiceprint of a Dr. Smith that works at the clinical environment, the role assigned 402 to encounter participant 226 by automated clinical documentation process 10 may be "doctor".

The process of assigning 402 a role to the encounter participants (e.g., encounter participants 226, 228, 230, 242) may be repeated by automated clinical documentation process 10 until all of the encounter participants (e.g., encounter participants 226, 228, 230, 242) are assigned 402 a role.

As discussed above, automated clinical documentation process 10 may be configured to process 302 the encounter information (e.g., machine vision encounter information 102 and/or audio encounter information 106) to generate an encounter transcript (e.g., encounter transcript 234). Accordingly, the text of the encounter transcript (e.g., encounter transcript 234) may be examined to see if the vocabulary being used by the encounter participant (e.g., encounter participants 226, 228, 230, 242) is associated with e.g., a doctor. For example, if the participant (e.g., encounter participant 226) is saying phrases such as "Where does it hurt?" and "How long have you had this pain?", the role assigned 402 to encounter participant 226 by automated clinical documentation process 10 may be "doctor".

When processing 302 the encounter information (e.g., machine vision encounter information 102 and/or audio encounter information 106) to generate an encounter transcript (e.g., encounter transcript 234), automated clinical documentation process 10 may process 504 the encounter information (e.g., machine vision encounter information 102 and/or audio encounter information 106) to compartmentalize the encounter information (e.g., machine vision encounter information 102 and/or audio encounter information 106) into a plurality of encounter stages.

As discussed above, a patient encounter (e.g., a visit to a doctor's office) may be divided into various portions, examples of which may include but are not limited to: a pre-visit (e.g., check in) portion, one or more examination portions (e.g., while meeting with the doctor, while vital signs and statistics are obtained, and while imaging is performed), and a post-visit (e.g., check out) portion.

Specifically and by examining the encounter information (e.g., machine vision encounter information 102 and/or audio encounter information 106), automated clinical documentation process 10 may compartmentalize the encounter information (e.g., machine vision encounter information 102 and/or audio encounter information 106) into a plurality of encounter stages (e.g., a pre-visit portion, one or more examination portions, and a post-visit portion.

For example and when processing 504 the encounter information (e.g., machine vision encounter information 102 and/or audio encounter information 106) to compartmentalize the encounter information (e.g., machine vision encounter information 102 and/or audio encounter information 106) into a plurality of encounter stages, automated clinical documentation process 10 may examine the encounter information (e.g., machine vision encounter information 102 and/or audio encounter information 106) to e.g., determine:

if the participant is sitting on an examination table or in a patient chair, which may be indicative of this portion of the encounter information being associated with an examination portion of the patient encounter (e.g., a visit to a doctor's office);

if the participant is performing "patient tasks" (e.g., being examined with a stethoscope, and having blood pressure readings taken), which may be indicative of this portion of the encounter information being associated with an examination portion of the patient encounter (e.g., a visit to a doctor's office);

if the participant is performing "doctor tasks" (e.g., examining someone with a stethoscope, and taking blood pressure readings), which may be indicative of this portion of the encounter information being associated with an examination portion of the patient encounter (e.g., a visit to a doctor's office);

if the participant is sitting at a reception desk, which may be indicative of this portion of the encounter information being associated with a pre-visit (e.g., check in) portion of the patient encounter (e.g., a visit to a doctor's office); and if the participant is sitting at a discharge desk, which may be indicative of this portion of the encounter information being associated with a post-visit (e.g., check out) portion of the patient encounter (e.g., a visit to a doctor's office).

Figure 9:
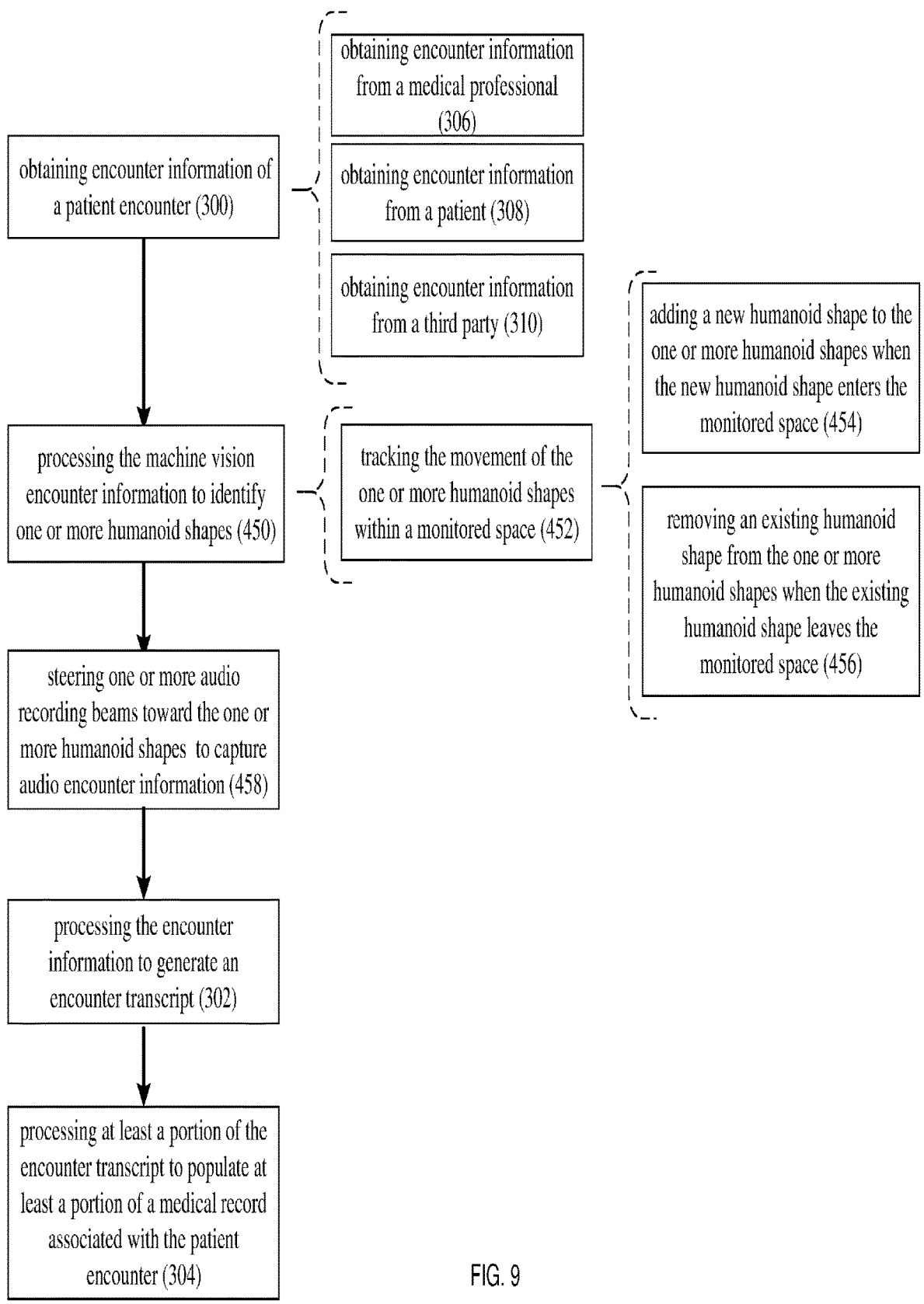
FIG. 9 is a flow chart of another implementation of the automated clinical documentation process of FIG. 1.

Video-Enhanced Beam Forming:

Automated clinical documentation process 10 may be configured to perform video-enhanced beam forming within monitored space 130. Accordingly and referring also to FIG. 9, automated clinical documentation process 10 may be configured to obtain 300 encounter information of a patient encounter (e.g., a visit to a doctor's office), wherein (and as discussed above) this encounter information may include machine vision encounter information 102 and/or audio encounter information 106.

As discussed above and when obtaining 300 encounter information (e.g., machine vision encounter information 102 and/or audio encounter information 106), automated clinical documentation process 10 may: obtain 306 encounter information (e.g., machine vision encounter information 102 and/or audio encounter information 106) from a medical professional (e.g., encounter participant 226); obtain 308 encounter information (e.g., machine vision encounter information 102 and/or audio encounter information 106) from a patient (e.g., encounter participant 228); and/or obtain 310 encounter information (e.g., machine vision encounter information 102 and/or audio encounter information 106) from a third party (e.g., encounter participant 230).

As discussed above, automated clinical documentation process 10 may process 450 the machine vision encounter information (e.g., machine vision encounter information 102) to identify one or more humanoid shapes. As discussed above, examples of machine vision system 100 generally (and ACD client electronic device 34 specifically) may include but are not limited to one or more of an RGB imaging system, an infrared imaging system, an ultraviolet imaging system, a laser imaging system, a SONAR imaging system, a RADAR imaging system, and a thermal imaging system).

As discussed above, ACD compute system 12 may be configured to access one or more datasources 118 (e.g., plurality of individual datasources 120, 122, 124, 126, 128), wherein examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

Accordingly and when processing 450 the machine vision encounter information (e.g., machine vision encounter information 102) to identify one or more humanoid shapes, automated clinical documentation process 10 may be configured to compare the humanoid shapes defined within one or more datasources 118 to potential humanoid shapes within the machine vision encounter information (e.g., machine vision encounter information 102).

The humanoid shapes defined within one or more datasources 118 may be defined with one or more humanoid models generated using e.g., various known machine learning techniques. For example, video-based data of participants within numerous patient encounters may be processed by such a machine learning process so that such humanoid models may be defined.

As discussed above, when processing 450 the machine vision encounter information (e.g., machine vision encounter information 102) to identify one or more humanoid shapes, automated clinical documentation process 10 may track 452 the movement of the one or more humanoid shapes within the monitored space (e.g., monitored space 130). For example and when tracking 452 the movement of the one or more humanoid shapes within monitored space 130, automated clinical documentation process 10 may add 454 a new humanoid shape to the one or more humanoid shapes when the new humanoid shape enters the monitored space (e.g., monitored space 130) and/or may remove 456 an existing humanoid shape from the one or more humanoid shapes when the existing humanoid shape leaves the monitored space (e.g., monitored space 130).

Accordingly and as discussed above, if a lab technician (e.g., encounter participant 242) temporarily enters monitored space 130 to chat with encounter participant 230, automated clinical documentation process 10 may add 454 encounter participant 242 to the one or more humanoid shapes being tracked 452. Further and as discussed above, if the lab technician (e.g., encounter participant 242) leaves monitored space 130 after chatting with encounter participant 230, automated clinical documentation process 10 may remove 456 encounter participant 242 from the one or more humanoid shapes being tracked 452.

Also and when tracking 452 the movement of the one or more humanoid shapes within monitored space 130, automated clinical documentation process 10 may monitor the trajectories of the various humanoid shapes within monitored space 130. Accordingly, assume that when leaving monitored space 130, encounter participant 242 walks in front of (or behind) encounter participant 226. As automated clinical documentation process 10 is monitoring the trajectories of (in this example) encounter participant 242 (who is e.g., moving from left to right) and encounter participant 226 (who is e.g., stationary), when encounter participant 242 passes in front of (or behind) encounter participant 226, the identities of these two humanoid shapes may not be confused by automated clinical documentation process 10.

Accordingly and once the one or more humanoid shapes are identified by automated clinical documentation process 10 (in the manner described above), automated clinical documentation process 10 may steer 458 one or more audio recording beams (e.g., audio recording beams 220, 222, 224) toward the one or more humanoid shapes (e.g., encounter participants 226, 228, 230) to capture audio encounter information (e.g., audio encounter information 106).

As discussed above, automated clinical documentation process 10 (via modular ACD system 54 and/or audio recording system 104) may utilize one or more of the discrete audio acquisition devices (e.g., audio acquisition devices 202, 204, 206, 208, 210, 212, 214, 216, 218) to form an audio recording beam. For example, modular ACD system 54 and/or audio recording system 104 may be configured to utilize various audio acquisition devices to form:

- audio recording beam 220, thus enabling the capturing of audio (e.g., speech) produced by encounter participant 226 (as audio recording beam 220 is pointed to (i.e., directed toward) encounter participant 226);
- audio recording beam 222, thus enabling the capturing of audio (e.g., speech) produced by encounter participant 228 (as audio recording beam 222 is pointed to (i.e., directed toward) encounter participant 228); and/or
- audio recording beam 224, thus enabling the capturing of audio (e.g., speech) produced by encounter participant 230 (as audio recording beam 224 is pointed to (i.e., directed toward) encounter participant 230).

Once obtained, automated clinical documentation process 10 may process 302 the encounter information (e.g., machine vision encounter information 102 and/or audio encounter information 106) to generate encounter transcript 234 and may process 304 at least a portion of encounter transcript 234 to populate at least a portion of a medical record (e.g., medical record 236) associated with the patient encounter (e.g., a visit to a doctor's office).

General:

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
    obtaining encounter information of a patient encounter, wherein the encounter information includes machine vision encounter information;
    processing the encounter information to identify a speaker within the patient encounter, wherein processing the encounter information to identify the speaker within the patient encounter includes comparing the machine vision encounter information of the encounter information to one or more humanoid models;
    determining that a first encounter participant is speaking using the one or more humanoid models;
    steering one or more audio recording beams toward the first encounter participant based upon, at least in part, determining that the first encounter participant is speaking;
    processing the encounter information to generate an encounter transcript;
    processing the machine vision encounter information of the encounter information to associate a first portion of the encounter information with the first encounter participant; and
    processing at least a portion of the encounter transcript to populate at least a portion of a medical record associated with the patient encounter.

2. The computer-implemented method of claim 1 wherein the one or more humanoid models includes a speaking humanoid model of the first encounter participant and a listening humanoid model of the first encounter participant.

3. The computer-implemented method of claim 1 wherein the encounter information further includes audio encounter information.

4. The computer-implemented method of claim 2 wherein steering the one or more audio recording beams toward the first encounter participant is based upon, at least in part, determining that the first encounter participant is speaking using the speaking humanoid model.

5. The computer-implemented method of claim 1 further comprising assigning a first role to the first encounter participant in the encounter transcript based upon the machine vision encounter information.

6. The computer-implemented method of claim 5 wherein the first role is one of a medical professional, a patient, and a third party.

7. The computer-implemented method of claim 1 wherein processing the encounter information to generate an encounter transcript includes:
    processing the encounter information to compartmentalize the encounter information into a plurality of encounter stages.

8. A computer program product residing on a non-transitory computer readable medium having a plurality of instructions stored thereon which, when executed by a processor, cause the processor to perform operations comprising:
    obtaining encounter information of a patient encounter, wherein the encounter information includes machine vision encounter information;
    processing the encounter information to identify a speaker within the patient encounter, wherein processing the encounter information to identify the speaker within the patient encounter includes comparing the machine vision encounter information of the encounter information to one or more humanoid models;
    determining that a first encounter participant is speaking using the one or more humanoid models;
    steering one or more audio recording beams toward the first encounter participant based upon, at least in part, determining that the first encounter participant is speaking;
    processing the encounter information to generate an encounter transcript;
    processing the machine vision encounter information of the encounter information to associate a first portion of the encounter information with the first encounter participant; and
    processing at least a portion of the encounter transcript to populate at least a portion of a medical record associated with the patient encounter.

9. The computer program product of claim 8 wherein the one or more humanoid models includes a speaking humanoid model of the first encounter participant and a listening humanoid model of the first encounter participant.

10. The computer program product of claim 8 wherein the encounter information further includes audio encounter information.

11. The computer program product of claim 9 wherein steering the one or more audio recording beams toward the first encounter participant is based upon, at least in part, determining that the first encounter participant is speaking using the speaking humanoid model.

12. The computer program product of claim 8 further comprising assigning a first role to the first encounter participant in the encounter transcript based upon the machine vision encounter information.

13. The computer program product of claim 12 wherein the first role is one of a medical professional, a patient, and a third party.

14. The computer program product of claim 8 wherein processing the encounter information to generate an encounter transcript includes:
processing the encounter information to compartmentalize the encounter information into a plurality of encounter stages.

15. A computing system including a processor and memory configured to perform operations comprising:
obtaining encounter information of a patient encounter, wherein the encounter information includes machine vision encounter information;
processing the encounter information to identify a speaker within the patient encounter, wherein processing the encounter information to identify the speaker within the patient encounter includes comparing the machine vision encounter information of the encounter information to one or more humanoid models;
determining that a first encounter participant is speaking using the one or more humanoid models;
steering one or more audio recording beams toward the first encounter participant based upon, at least in part, determining that the first encounter participant is speaking;
processing the encounter information to generate an encounter transcript;
processing the machine vision encounter information of the encounter information to associate a first portion of the encounter information with the first encounter participant; and
processing at least a portion of the encounter transcript to populate at least a portion of a medical record associated with the patient encounter.

16. The computing system of claim 15 wherein the one or more humanoid models includes a speaking humanoid model of the first encounter participant and a listening humanoid model of the first encounter participant.

17. The computing system of claim 15 wherein the encounter information further includes audio encounter information.

18. The computing system of claim 16 wherein steering the one or more audio recording beams toward the first encounter participant is based upon, at least in part, determining that the first encounter participant is speaking using the speaking humanoid model.

19. The computing system of claim 15 further comprising assigning a first role to the first encounter participant in the encounter transcript based upon the machine vision encounter information.

20. The computing system of claim 15 wherein processing the encounter information to generate an encounter transcript includes:
processing the encounter information to compartmentalize the encounter information into a plurality of encounter stages.

* * * * *